United States Patent [19]
Hogendijk et al.

[11] Patent Number: 6,051,007
[45] Date of Patent: Apr. 18, 2000

[54] STERNAL CLOSURE DEVICE AND INSTRUMENTS THEREFOR

[75] Inventors: Mike Hogendijk, Palo Alto, Calif.; Troy Chapman, Avilla, Ind.

[73] Assignee: Corvascular, Inc., Palo Alto, Calif.

[21] Appl. No.: 09/033,219

[22] Filed: Mar. 2, 1998

[51] Int. Cl.[7] ................................................. A61B 17/04
[52] U.S. Cl. .......................... 606/151; 606/215; 606/216
[58] Field of Search .................................... 606/151, 215, 606/216

[56] References Cited

U.S. PATENT DOCUMENTS

| | | |
|---|---|---|
| D. 309,350 | 7/1990 | Sutherland et al. . |
| 408,080 | 7/1889 | Carrol .................................... 606/216 |
| 3,385,299 | 5/1968 | Roy ......................................... 606/216 |
| 3,473,528 | 10/1969 | Mishkin et al. ........................ 606/215 |
| 3,971,384 | 7/1976 | Hasson .................................... 606/216 |
| 4,201,215 | 5/1980 | Crossett . |
| 4,279,248 | 7/1981 | Gabbay . |
| 4,512,346 | 4/1985 | Lemole . |
| 4,583,541 | 4/1986 | Barry . |
| 4,730,615 | 3/1988 | Sutherland et al. . |
| 4,794,675 | 1/1989 | Bisconti . |
| 4,802,477 | 2/1989 | Gabbay . |
| 4,813,416 | 3/1989 | Pollak et al. . |
| 4,896,668 | 1/1990 | Popoff et al. . |
| 5,139,498 | 8/1992 | Astudillo Ley . |
| 5,163,598 | 11/1992 | Peters et al. . |
| 5,263,973 | 11/1993 | Cook ....................................... 606/215 |
| 5,318,566 | 6/1994 | Miller . |
| 5,330,489 | 7/1994 | Green et al. . |
| 5,339,870 | 8/1994 | Green et al. . |
| 5,356,412 | 10/1994 | Golds et al. . |
| 5,356,417 | 10/1994 | Golds . |
| 5,423,821 | 6/1995 | Pasque . |

OTHER PUBLICATIONS

Brown et al., "Improved sternal fixation in the transsternal bilateral thoracotomy incision" *J. Thorac. Cardiovasc. Surg.* (1996)112(1). Abstract.

Hendrickson et al., "Sternal plating for the treatment of sternal nonunion" *Ann. Thorac. Surg.* (1996)62:512–518.

*Primary Examiner*—Gary Jackson
*Attorney, Agent, or Firm*—Morrison & Foerster LLP

[57] ABSTRACT

A sternal closure device comprising first and second clamps. The first and second clamps have a generally tubular portion and the second clamp has a portion that is slidably receivable in the tubular portion, and a lock configured to retain said second clamp within said first clamp. A surgical instrument for laterally moving opposed sternal clamps toward one another is also disclosed. The instrument comprises first and second grasping members generally linearly slidably coupled to one another.

44 Claims, 17 Drawing Sheets

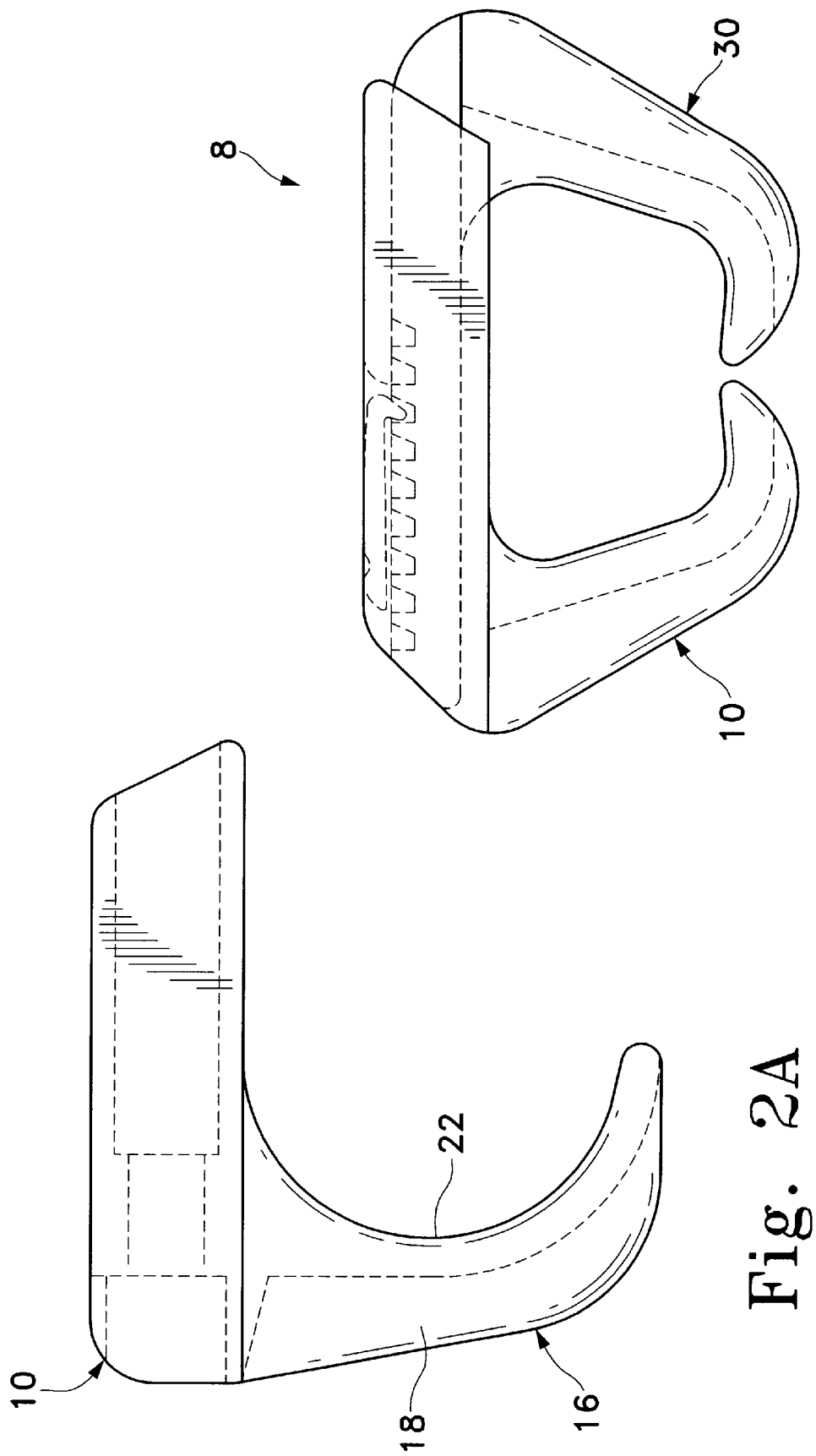

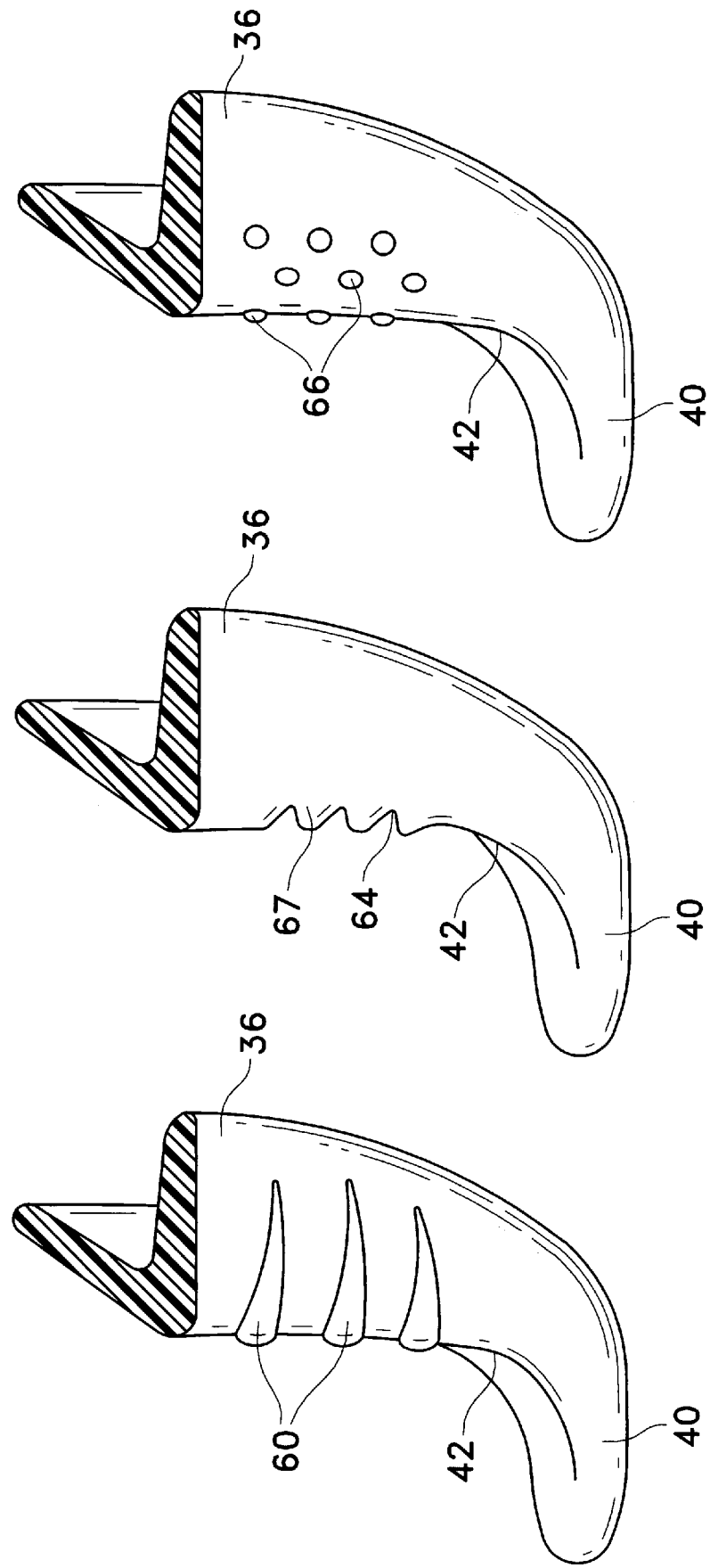

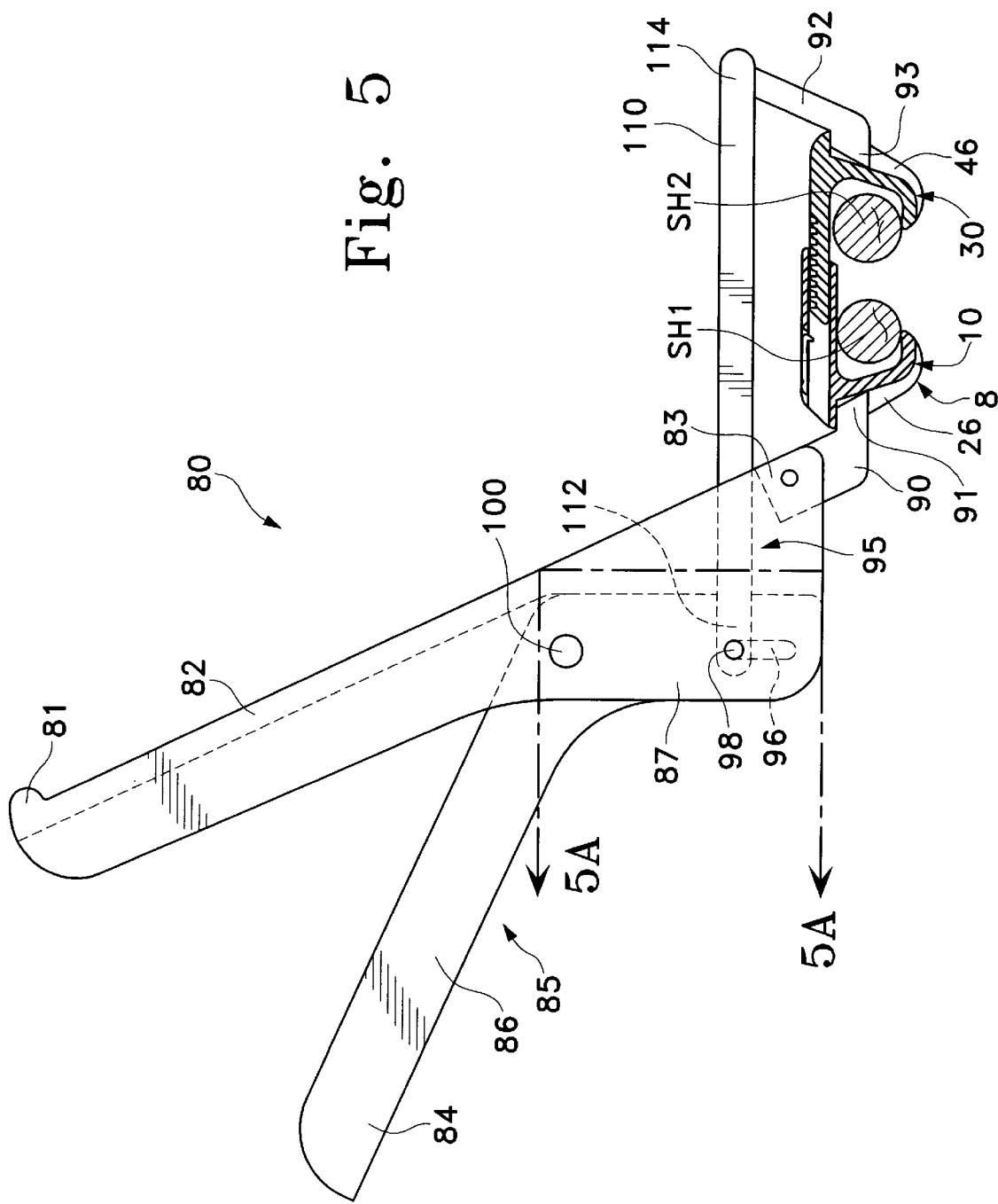

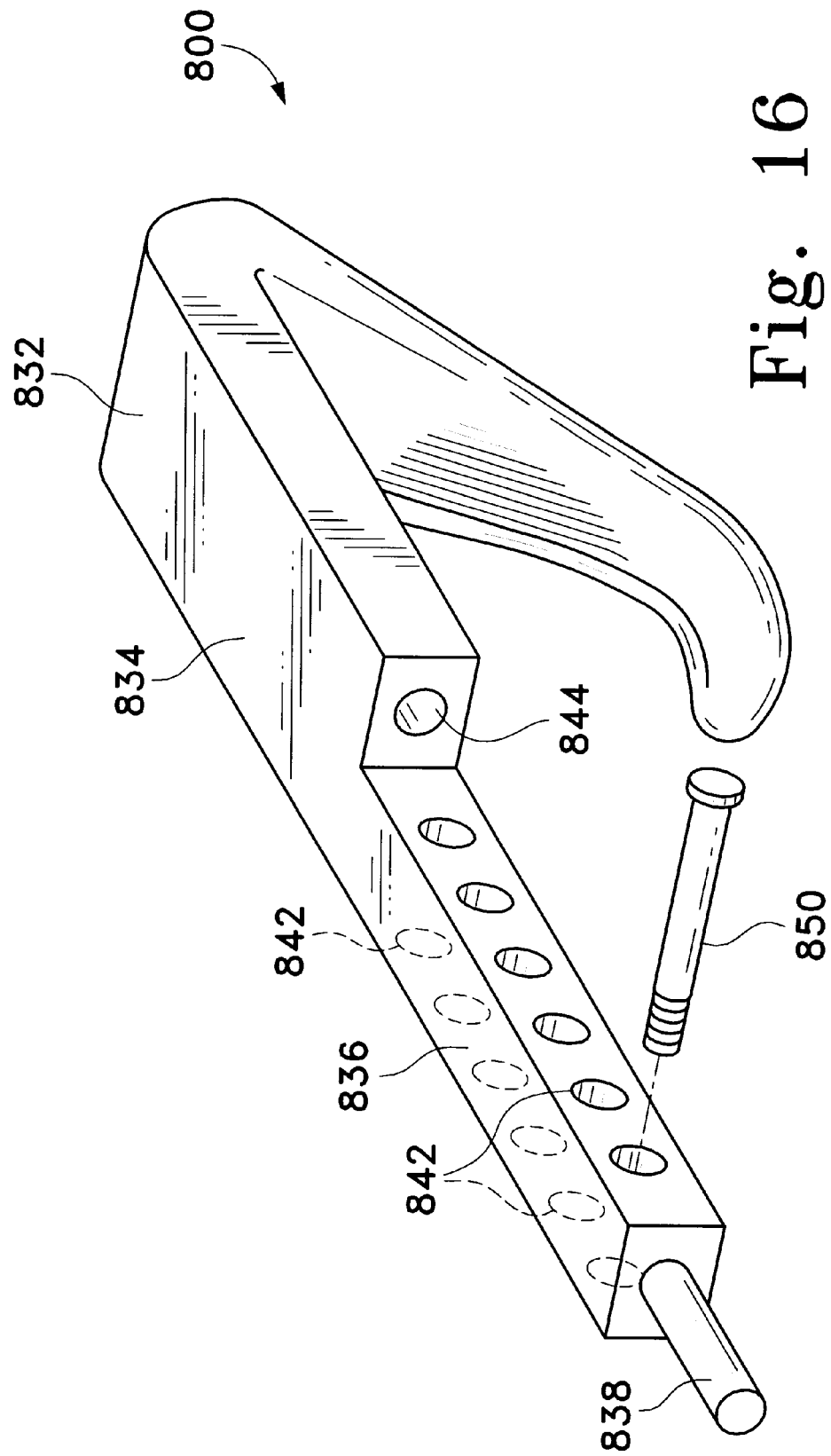

STERNAL CLOSURE DEVICE AND INSTRUMENTS THEREFOR

FIELD OF THE INVENTION

The present invention relates generally to surgical devices, and more particularly to devices and methods for reapproximating the sternal halves of a patient's severed sternum following a partial or median sternotomy.

BACKGROUND OF THE INVENTION

Various types of surgical procedures are currently performed to investigate, diagnose, and treat diseases involving a tissue or organs located in a patient's thoracic cavity (e.g., the heart, lungs, and the like). Using current techniques, many of those procedures typically require a partial or median sternotomy to gain access into the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs or tissues.

Following the surgical procedure within the thoracic cavity, the two severed sternal halves must be reapproximated (closed). Traditionally, the sternal halves have been reapproximated with stainless steel wires which are wrapped around or through the sternal halves so as to exert medial compression thereon and twisted together to approximate the sternum. Other methods of sternum repair include the use of band or strap assemblies. Such assemblies typically include a locking mechanism, which secures a strap in a closed looped configuration about the sternum positions. While utilization of steel wires and strap assemblies have been widely accepted for sternum repair, these devices present a number of disadvantages. Steel wires can and do break, and provide insufficient (non-uniform) clamping force resulting in sternal nonunion. Steel wires are difficult to maneuver and place around the sternum. The cut ends of the steel wires are also sharp and can pierce through the surgeon's gloves or fingers. In addition, the small diameter of the steel wires can cause the wires to migrate into or through the tissue surrounding the sternum region or into the sternal bone itself over time. This can lead to significant patient pain and discomfort in addition to slowing the postoperative recovery and increasing the risk of sternal infection. Moreover, the strap mechanisms of band assemblies are often relatively structurally complex and are difficult to precisely apply about the sternum. There are also healing problems associated with the use of steel wires and band assemblies due to improper forces exerted by these devices which can cause unwanted bone movements leading to raking and rubbing of surrounding tissue or bone.

Several other techniques of sternal reapproximation have been proposed both for primary closure following a median sternotomy and for reclosure following post-operative emergency surgical procedures. One such sternal fixation device is described in Brown, R. P., Esmore, D. S., and Lawson, C., Improved Sternal Fixation in the Transternal Bilateral Thoracotomy Incision, J. Thoracic Cardiovascular Surg. 1996, Volume 112, number 1, the entire contents of which are incorporated herein by reference. The device described therein is composed of two plates, one anterior and one posterior to the sternum, that are fixed to each other and to the sternum by means of screws into internally threaded posts positioned in predrilled holes through the bone on either side of the sternotomy. This device, and others similar to it, are not optimal, however, because they require direct fixation of the plates to the bone with screws. This makes reentry into the thoracic cavity through the sternotomy extremely difficult if a medical emergency arises during the surgical procedure or post-operative requiring relatively quick access to the organs and/or tissues within the patient's thoracic cavity.

To overcome the problems inherent in direct fixation devices, another technique of sternal reapproximation has been proposed which employs overlapping sternal plates which can be removably joined to one another. In Hendrickson, S. C., Koger, K. E., Morea, C. J., Aponte, R. L., Smith, P. K., and Levin, S. L., Sternal Plating for the Treatment of Sternal Nonunion, Ann. Thor. Surg. 1996:62:512–8, the entire contents of which are incorporated by reference herein, a separable sternal clamping device is disclosed which includes a pair of opposed stainless steel sternal clamp plates which include respective generally J or C-shaped sternal engagement legs. The sternal clamp plates are laterally adjustable relative to one another but can be rigidly joined by, for example, a set of machine screws. The threaded coupling of the machine screws with the sternal plates removably secures the plates one to another in overlapping relationship without lateral shifting occurring over time, allowing easy reopening of the sternum if necessary.

Other improvements to sternal clamping devices and methods for sternal reapproximation are needed which are easily assembled, and which provide a stable and uniform clamping force and a well-approximated closure that allows bone healing to occur. The devices and methods should facilitate reopening of the sternum if necessary, e.g., in case of a medical emergency requiring the surgeon to have access to the patient's thoracic cavity. Preferably, the devices should be made from a biocompatible, radiolucent material which facilitates post-operative radioscopic viewing of the thoracic cavity. The lateral dimension between the clamp members of the devices should also be adjustable to fit a particular patient's sternum. New surgical tools are also required to assist the surgeon in properly tensioning the clamping device during the reapproximation procedure and for measuring the thickness of the sternal halves so that the surgeon can select the optimum sizes of the clamp member pairs for reapproximating the sternum.

SUMMARY OF THE INVENTION

The present invention provides improved devices and methods for reapproximating the sternal halves of a patient's sternum following a median or partial sternotomy that facilitates ready access to the thoracic cavity during or after a medical procedure (e.g., in the case of a medical emergency) and which overcomes sternal nonunion problems inherent in previous sternal closure devices. Broadly, the present invention is embodied in a pair of opposed sternal clamp members that can be detachably secured to one another.

According to a first aspect of the invention, a sternal closure device comprises first and second clamps. The first clamp has a generally tubular portion and the second clamp has a portion that is slidably receivable in the tubular portion. A lock is provided to secure the second clamp within the first clamp.

According to a second aspect of the invention, the first clamp of the sternal device has an elongated portion and the second clamp has an elongated portion adapted for engaging the elongated portion of the first clamp without substantially overlapping the first clamp.

A surgical instrument of the present invention is for laterally moving opposed sternal clamps toward one another. The instrument generally comprises first and second grasping members generally linearly slidably coupled to one another.

A sternum measuring instrument of the present invention comprises a generally L-shaped member having at least two surfaces adapted for engaging a person's sternum. The instrument includes indicia along one side thereof.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

FIG. 2A is a side view of an alternative embodiment of an engagement leg of one of the opposed clamp members of FIG. 1;

FIG. 3 is a side view of the sternal closure device of FIG. 2 shown in an assembled state;

FIGS. 4A–C are perspectives of engagement legs of one of the clamp members of the sternal closure device showing alternative embodiments of gripping surfaces on the engagement surface of the engagement leg;

FIG. 5 is a side view of a surgical tool shown in engagement with opposed clamp members;

FIG. 13A is a top view of the closure device of FIG. 13;

FIG. 16 is a perspective of an alternative embodiment of the sternal closure device of FIG. 15 showing one of a pair of identical clamp members in a disassembled state which is adapted to be removably joined to another structurally identical clamp member in a side-by-side relationship.

DETAILED DESCRIPTION OF THE INVENTION

Figure 1:
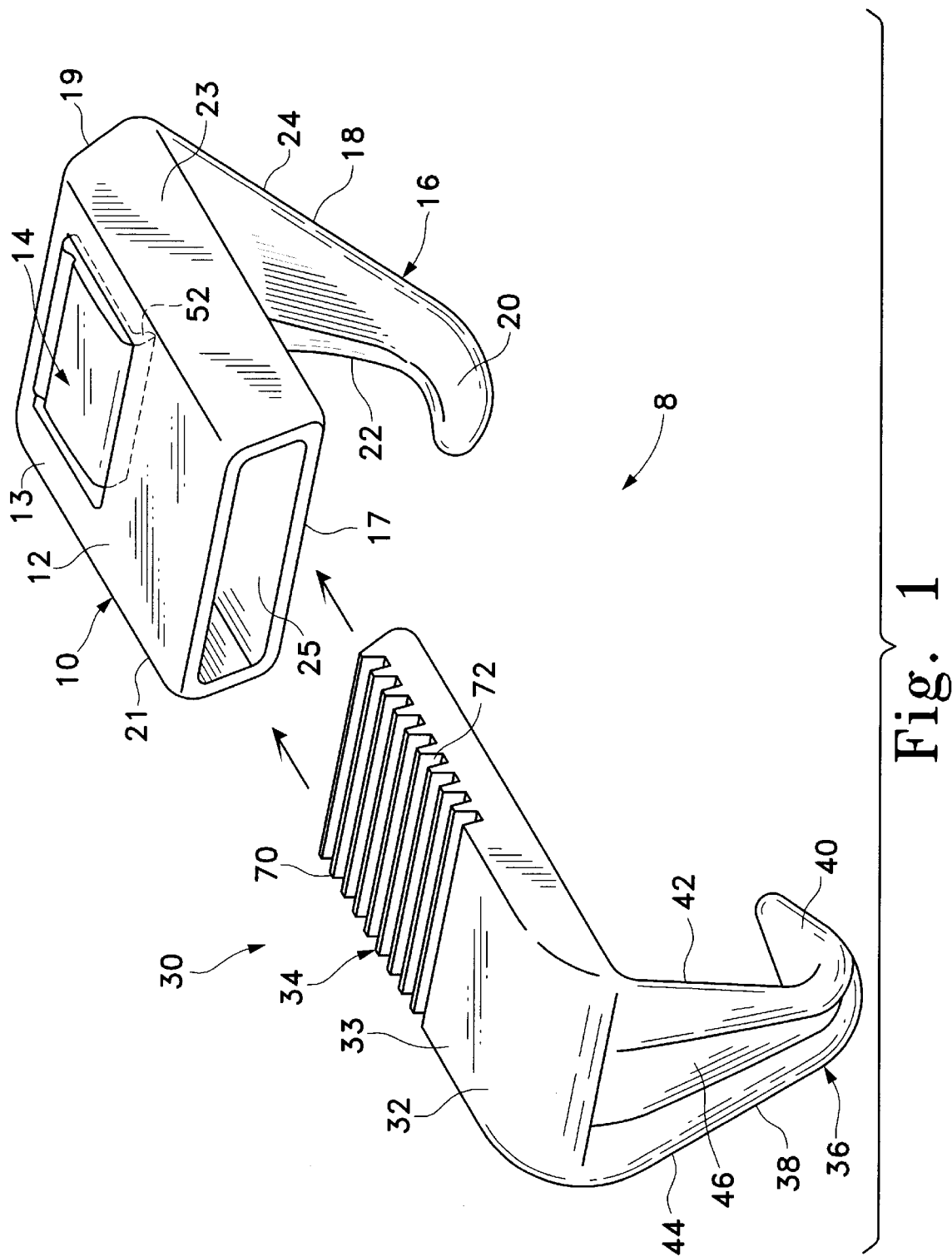
FIG. 1 is a perspective of a sternal closure device constructed in accordance with the principles of the present invention showing the opposed clamp members in a disassembled state.
Figure 2:
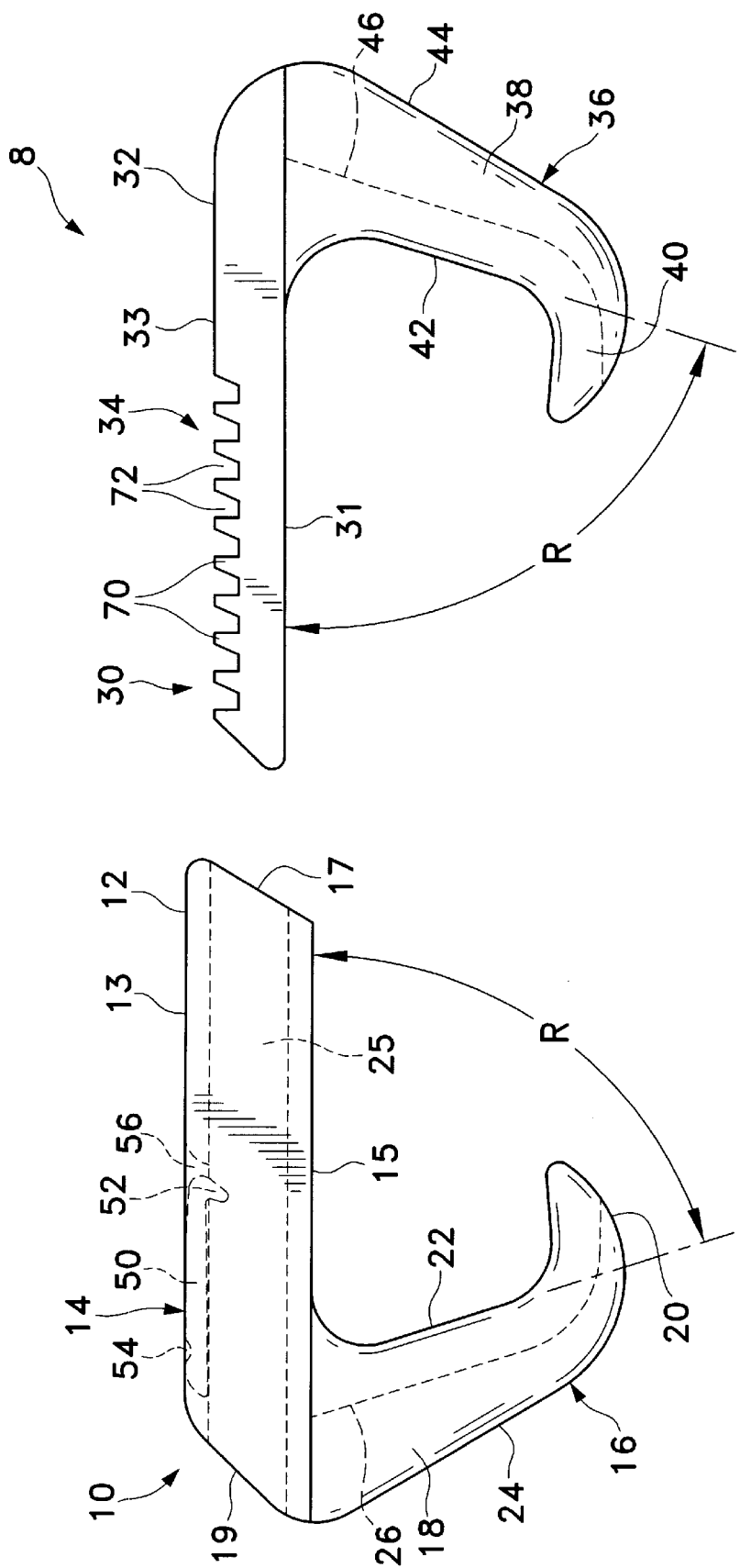
FIG. 2 is a side view of the sternal closure device of FIG. 1.

Referring to the drawings wherein like numerals indicate like elements one embodiment of a sternal closure device according to the present invention is shown in FIGS. 1–3 and generally designated with reference numeral 8. As shown therein, sternal closure device 8 includes a pair of opposed clamp members (or clamps) 10, 30. Although other materials may be used, clamp members 10, 30 preferably are made from a radiolucent, biocompatible material such as polysulfone or Ultra High Molecular Weight Polyethylene ("UHMWPE"). The radiolucent character of clamp members 10, 30 facilitates post-operative radioscopic viewing of the treatment site within the patient's thoracic cavity, which can be obscured by bulky radio-opaque sternal approximators. Clamp members 10, 30 each comprise respective elongate body portions 12, 32 which as shown may be planar and are integrally connected to or formed with respective engagement legs 16, 36. Engagement legs 16, 36 each include a respective spine portion 18, 38 having an inner sternal engagement surface 22, 42, respectively, for engaging and gripping about the respective sternal halves of a patient's severed sternum, as well as an outer surface 24, 44, respectively. Spine portions 18, 38 terminate at their lower ends in respective foot portions 20, 40, which as shown may be substantially planar. Foot portions 20, 40 are configured to be slightly spaced from the posterior surface of the sternum in the normal configuration of the assembled sternal closure device 8 about the reapproximated sternum. Foot portions 20, 40 are adapted to passively engage the posterior surface of the sternum in the event that the sternum tends to shift within the assembled sternal closure device 8 under the action of medial forces applied to the sternum. In this way, foot portions 20, 40 generally enhance the overall circumferential support about the sternum and reduce the potential likelihood that the reapproximated sternum will separate itself from the assembled sternal closure device 8.

Preferably, engagement surfaces 22, 42 of spine portions 18, 38 are substantially straight as shown in FIG. 2, although the engagement surfaces also could be generally curved into a general C-shaped configuration as shown by the spine portion 18 of engagement leg 16 of the first clamp member 10 in FIG. 2A. Preferably, where spine portions 18, 38 have a substantially straight configuration, the spine portions are configured to extend at an angle "R" relative to body portions 12, 32, respectively, as best seen in FIG. 2. The angle R between respective body portions 12, 32 and spine portions 18, 38 is preferably between 45 and 90 degrees, more preferably between 70 and 80 degrees, and most preferably about 75 degrees. This particular angular orientation between the respective body portions and spine portions is desirable to secure the sternal halves within the grasp of the clamp members 10, 30 because, in the assembled state of the clamp members, any medial forces exerted on the sternum will cause the respective sternal halves to be urged upwards away from foot portions 20, 40 and firmly within the grasp of clamp members 10, 30.

A respective vertical groove 26 and 46 is provided in each outer surface 24, 44 of respective spine portions 18, 38. Grooves 26, 46 extend at one end from the upper portion of spine portions 18, 38, and terminate at the foot portions 20, 40 at their respective other ends. Vertical grooves 26, 46 are adapted to permit the opposed grasping members of a surgical tool, such as grasping members of 90, 92 of tool 80 as shown in FIG. 5, to engage clamp members 10, 30 therebetween. Thus, with the opposed grasping members 90, 92 so engaged, closing of the grasping members will cause the clamp members 10, 30 to be moved laterally towards one another as will be described in more detail below.

As shown in FIGS. 4A–C, sternal engagement surfaces 22, 42 of respective engagement legs 16, 36 may include alternative gripping surfaces to provide an improved holding force for gripping respective opposed sternal halves of the patient's severed sternum. For purposes of simplification, FIGS. 4A–C depict improved gripping surfaces only on engagement surface 42 of engagement leg 36 of second clamp member 30, although it is to be understood that like gripping surfaces also may be provided on engagement surface 22 of engagement leg 16. Referring to FIG. 4A, sternal engagement surface 42 of engagement leg 36 is provided with a plurality of protruding ribs 60 which taper downwards towards foot portion 40. The protrusions are integrally formed with the legs 16, 36. The ribs 60 could be rounded as shown or more pointed. Referring to FIG. 4B, sternal engagement surface 36 is provided with a plurality of teeth 62 defining a plurality of grooves 64 therebetween. FIG. 4C shows a further embodiment of an improved gripping surface in which engagement surface 36 has a plurality of small protrusions or mounds 66 which provide several contact surfaces which provide a greater friction surface area to help retain a sternal half against engagement surface 42. In addition to providing any one of the various types of mechanical friction configurations described above (or any combination thereof) to increase the gripping force of the sternal engagement surfaces 22, 42, the gripping surface of the sternal engagement surface 22, 42 could also be improved by applying a coating of silicone or like surface-tension enhancing material as conventional in the art, to the engagement surfaces 22, 42. The coating could be applied in a variety of ways, such as by spraying the engagement legs with the coating material, dipping the engagement legs in the material, sliding and expanding a sleeve of the material over the engagement legs, or by applying the material in any one of a variety of other ways as would be obvious to a person of ordinary skill in the art. Material forming engagement legs 16, 36 may also include one or more microscopic perforations or apertures (not shown) which provide increased ingrowth of tissue for anchoring the sternum to the engagement legs and enhancing the gripping force of the engagement legs.

Referring again to FIGS. 1–3, body portion 12 of clamp member 10 comprises top and bottom sides 13, 15, respectively, an open front and rear side 17, 19, respectively, and opposed longitudinal broad sides 21, 23, respectively, which together define a central recess 25 and form a tubular portion. The tubular portion may be rectangular, circular or various other shapes. Body portion 32 of clamp member 30 is sized to slide at least partially within recess 25 in body portion 12 of first clamp member 10. Body portion 32 may include a structural stiffener, such as a stainless steel stiffening rod (not shown), which extends within body portion 32 along its longitudinal axial length (central longitudinal axis). The structural stiffener provides enhanced rigidity to body portion 32 to counteract moment forces applied to body portion 32 in use of the device. A locking mechanism (securing means) is provided to rigidly and detachably secure body portion 32 of second clamp member 30 within body portion 12 of first clamp member 10.

As best seen in FIG. 2, in a first embodiment of the locking mechanism, clamp member 10 includes a lock member 14 which comprises a ratchet pawl 50 which is integrally connected to the top side 13 of body portion 12 at rear edge 54. Rear edge 54 of ratchet pawl 50 is slightly radiused inwards to allow ratchet pawl 50 to be more easily biased upwards as will be explained in greater detail below. Ratchet pawl 50 includes at least one ratchet tooth 52 at the opposite end of the ratchet pawl which extends inwardly within recess 25 and faces towards bottom side 15 of body portion 12. The second clamp member 30 comprises a catch member 34 which includes a plurality of ratchet teeth 70 which may be integral with and extend along an upper surface 33 of body portion 32. Ratchet teeth 70 define a plurality of grooves 72 between the teeth 70 and are configured to selectively engage ratchet tooth 52. As shown in FIG. 3, when the body portion 32 of second clamp member 30 partially slides within recess 25 of body portion 12 of clamp member 10, ratchet tooth 52 selectively engages with any one of the grooves 70 between ratchet teeth 72 to thereby secure the clamp members one to another at any one of a number of preselected relative lateral positions of the clamp members. As such, the lateral dimension between the opposed clamp members can be adjustably selected to fit a particular patient's sternum.

First clamp member 10 may further include detachment means to allow the clamp members 10, 30 to be quickly and easily separated from one another. Preferably, a small space 56 is provided between ratchet pawl 50 and top side 13 of body portion 12 which allows a surgeon to quickly and easily release the ratchet pawl 50 from engagement with catch member 34 by inserting a surgical instrument into the space 56 and biasing the ratchet pawl 50 upwards. The radiused rear edge 54 of ratchet pawl 50 facilitates upward movement of the pawl 50 by the surgeon by providing a region of reduced material to facilitate bending or flexing of the pawl. Thus, if there is any need to remove the device and quickly separate the clamp members from one another, ratchet pawl 50 may be simply disengaged from catch member 34 so that the clamp members can be separated laterally away from one another. Moreover, because the device preferably is fabricated from a plastic material, it can be easily cut away with standard surgical tools in an emergency situation, if necessary.

The sizes and cross-sectional shapes of the opposed clamp members 10, 30 can vary depending on the sizes and cross-sectional shapes of the sternal halves about which they are positioned, and preferably will be selected to provide a secure fit about the sternal halves to provide an optimum clamping force for reapproximating the sternum. Preferably, the thickness of body portion 12 (i.e., the distance between top and bottom sides 13, 15) is between about 6.0 to 7.0 mm, and the corresponding thickness of body portion 32 is between about 4.0 to 5.0 mm to provide a secure interlocking fit within body portion 12. The preferred width of body portion 12 (i.e., the distance between sides 21, 23) is between about 12.0 and 13.0 mm, and the corresponding preferred width of body portion 32 is between about 10.0 and 11.0 mm. The preferred width of engagement legs 16, 36 is preferably between about 6.0 and 7.0 mm. The clamp members 10, 30 can be machined or injection molded, as desired. These various dimensions of clamp members 10, 30 are in no way meant to limit the invention to only clamp members having those specific dimensions, and other suitable dimensions could be provided for clamp members 10, 30 without departing from the scope of time invention.

Generally, a patient's sternum will range in thickness from between about 8.0 mm to about 20.0 mm depending on the size of the person. To provide an optimum fit about any particular patient's sternum, the clamp members preferably will be provided in several different thickness sizes to fit a particular patient's sternum wherein the thickness of the clamp members is measured as the distance between an upper surface of the transverse foot portion 20 and a lower surface of the bottom side of body portion 12 of first clamp member 10. Typically, a surgeon will use between three to five pairs of opposed clamp members 10, 30 to secure the sternum. These clamp member pairs 10, 30 may be of the same or different thickness depending on the width of the sternum at the various locations along its axial length at which the clamp member pairs are positioned.

Figure 5A:
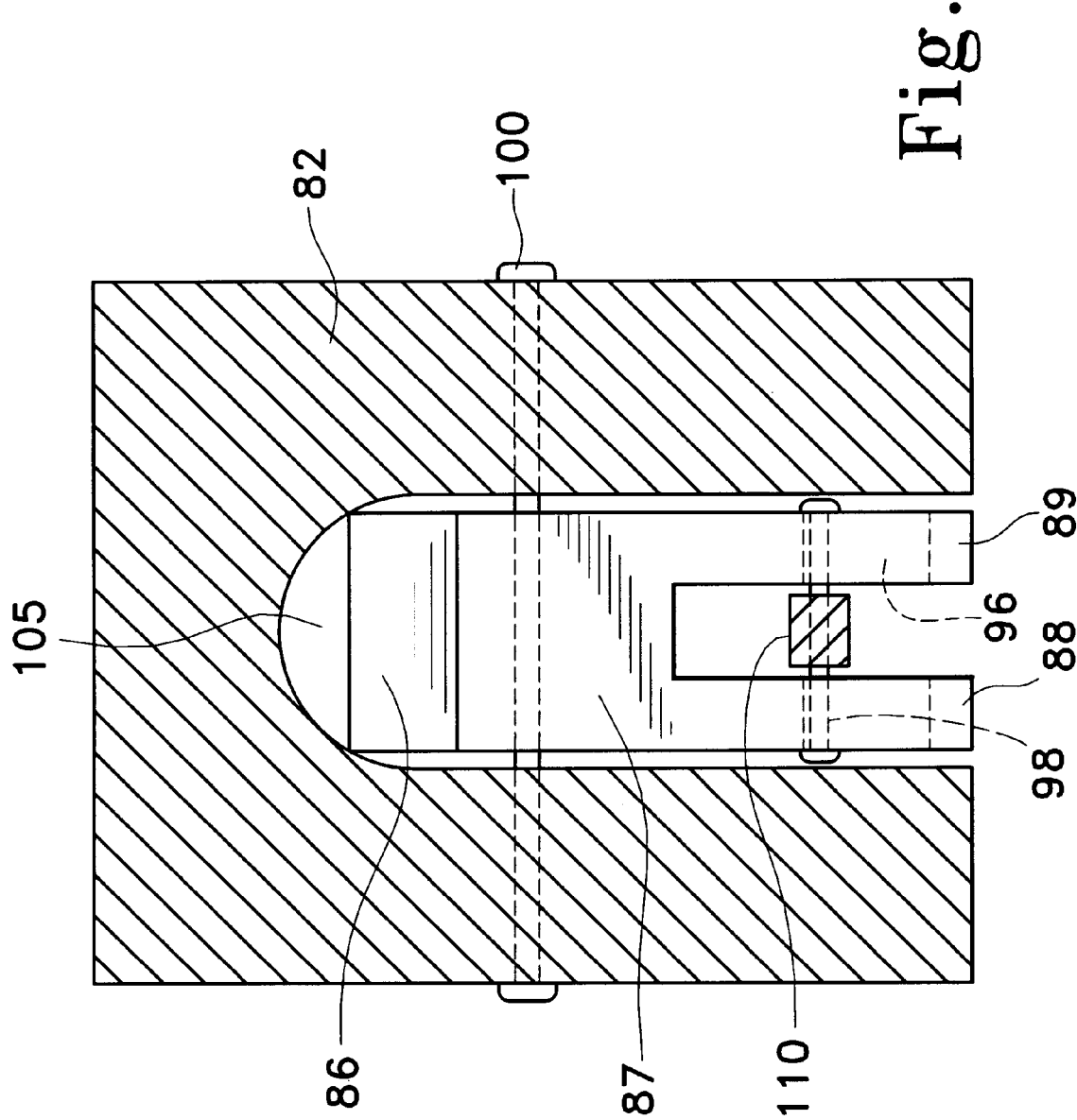
FIG. 5A is a cross-sectional view taken in the plane including line 5A—5A of FIG. 5.

A method for closing a sternum which has beer longitudinally severed for the purpose of gaining access to a patient's thoracic cavity will now be described with reference to FIGS. 5–6. Referring to FIG. 6A, a surgical instrument (tool or measurement device) 73 is shown according to the present invention. Tool or device 73 can be provided for determining the thickness of the sternal halves so that the surgeon can select the most appropriate size clamp member pairs 10, 30 to place about the sternal halves at various locations along the axial length of the sternal halves. Surgical tool 73 is generally L-shaped and comprises an elongate handle arm 74 which is integrally formed with or connected to an engagement leg 75 at one end of the handle arm. Handle arm 74 includes an inner sternal engagement surface 76 which is adapted to abut a surface of the sternal half, and an outer surface 77 which includes an appropriate scale 78 for measuring the thickness of the sternal half. The scale 78 provided on outer surface 77 of handle arm 74 can include various indicia of incremental measurements along the axial length of outer surface 77, such as a plurality of ruled lines indicating millimeters, centimeters, inches, etc. Engagement leg 75 is generally planar and extends substantially perpendicular to handle arm 74. Engagement leg 75 is sized and configured to be positioned about a respective sternal half of the sternum.

Figure 6:
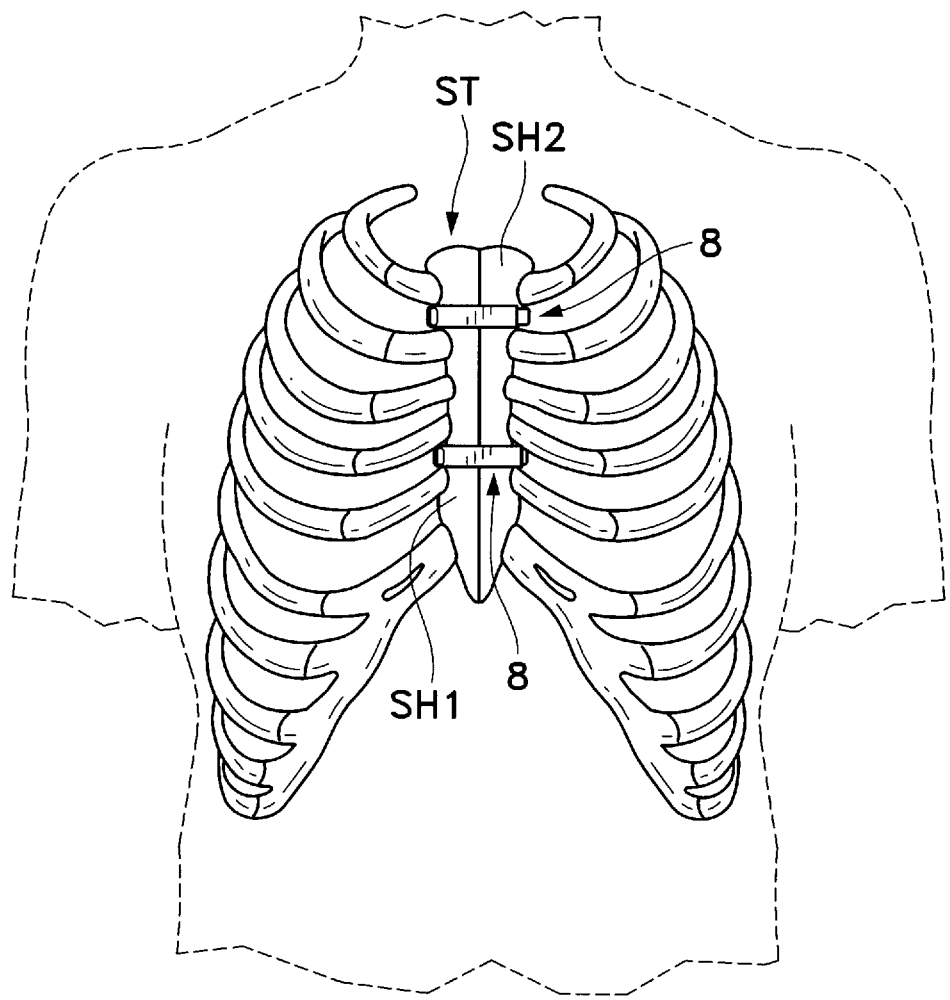
FIG. 6 is a front view of a sternum held in position to heal by one or more sets of opposed clamp members of the present invention.
Figure 6A:
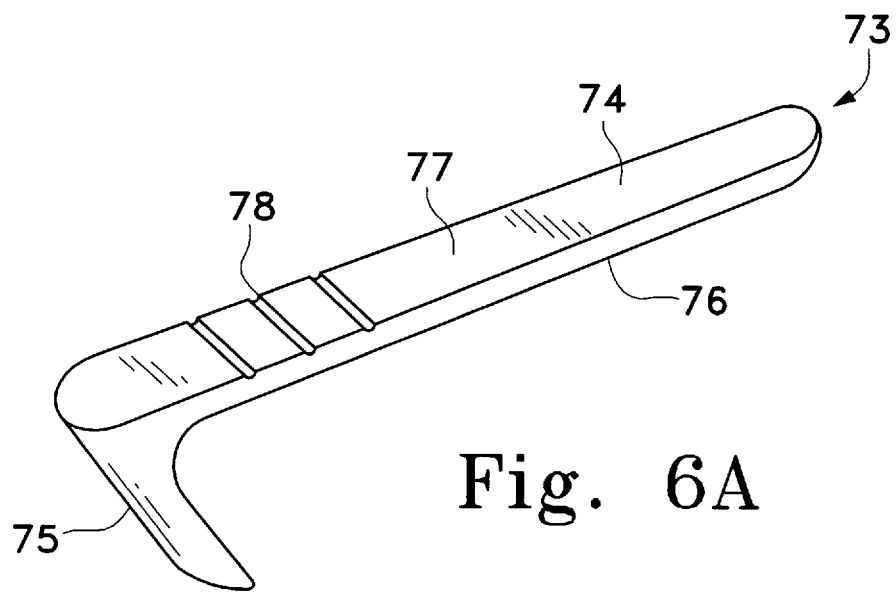
FIG. 6A is a perspective of a surgical tool for measuring the thickness of a sternal half of a patient's severed sternum following a median sternotomy.

In use of measurement device 73 for measuring the thickness of a sternal half at various locations along the axial length of the sternum, a surgeon will place engagement leg 75 through any desired intercostal space between the ribs of a patient's rib cage at the lateral border of one of the sternal halves SH1 or SH2 of FIG. 6. Engagement leg 75 engages the posterior surface of sternal half SH1 or SH2 as the measurement device 73 is rotated by the surgeon to a substantially perpendicular position relative to an axial length of the sternal half. This will allow the surgeon to view scale 78 on the outer surface 77 of handle arm 74 to allow him or her to determine the proper thickness of the sternal half and, thus, the appropriate corresponding size clamp member pairs 10, 30 to use at that location to reapproximate the sternal halves SH1 and SH2.

As shown in FIG. 5, once the appropriate size clamp member pairs 10, 30 are chosen by the surgeon, the surgeon will hook the respective sternal clamp members 10 and 30 laterally around the sternal halves SH1 and SH2, respectively, of the patient's severed sternum. A surgeon will then bring body portion 32 of clamp member 30 into interlocking relationship partially within the recess within body portion 12 of clamp member 10. To adjust the lateral dimension between the clamp members and securely adjust the sternal closure device 8 about a particular patient's sternum, a suitable surgical tensioning tool such as that generally designated with reference numeral 80 in FIG. 5 can be used by the surgeon.

Surgical tool 80 includes first and second grasping members 90, 92, respectively, which include respective grasping portions 91, 93. Grasping portions 91, 93 are configured to engage respective vertical grooves 26, 46 in the outer surface of spine portions 18, 38 of clamp members 10, 30. Surgical tool 80 further includes a first handle arm 82 which is oriented at an angle relative to an axial length of the assembled sternal closure device 8. First handle arm 82 has a proximal end 81 and a distal end 83. First grasping member 90 is fixedly connected to first handle arm 82 at distal end 83 of the handle arm. An actuator mechanism 85 is provided which includes a second handle arm 84 pivotally coupled to handle arm 82 via a coupling pushpin 100. Handle arm 84 includes an upper portion 86 and a lower portion 87. As best seen in FIG. 5A, the lower portion 87 of handle arm 84 is configured to be pivotable via push pin 100 within a U-shaped cut out-portion 105 in the distal portion of handle arm 82. Lower portion 87 of handle arm 84 has a fork-shaped configuration and includes first and second arms 88, 89, respectively, which terminate at respective free ends.

Actuator mechanism 85 further includes a link mechanism 95 which is configured to movably couple second handle arm 84 to second grasping member 92. Link mechanism 95 includes a rigid bar 110 having a proximal end 112 and a distal end 114. Second grasping member 92 is fixedly connected to bar 110 at the distal end 114 of the bar. A pin member 98 is connected to the bar 110 through an aperture in the proximal end 112 of the bar. The pin member 98 is configured to be slidably received within a vertically extending slot 96 through first and second arms 88, 89 of lower portion 87 of handle arm 84. Thus, as second handle arm 84 is rotated upwards towards first handle arm 82, the pin member 98 moves within vertical slot 96 which causes the bar 110 to move laterally in a horizontal plane. This will cause the second grasping member 92 to move laterally towards first grasping member 90. Optionally, the surgical tensioning tool 80 can include means for measuring the thickness of the opposed sternal halves. For example, the first handle arm 82 can include a transverse engagement leg (not shown) connected to the proximal end 81 of the handle arm 82. An appropriate measuring scale (not shown) can be provided on an external surface of the first handle arm 82. Thus, the optional engagement leg connected to the first handle arm 82 can be used to engage the posterior surface of a sternal half as the handle arm 82 is rotated by the surgeon to a substantially perpendicular position relative to an axial length of the sternal half. This will allow the surgeon to view the scale on the outer surface of handle arm 82.

As best seen in FIG. 5, during the reapproximation procedure, the surgeon will position the grasping members 90, 92 of surgical tool 80 about the outer surfaces of the clamp members 10, 30 so that the opposing grasping portions 91, 93 engage respective vertical grooves 26, 46 in the clamp members. The surgeon can then rotate second handle arm 84 upwards towards first handle arm 82 to force second clamp member 30 to move laterally towards first clamp member 10. This will force the ratchet tooth 52 of first clamp member 10 to move in and out of selective engagement with adjacent grooves 72 between ratchet teeth 70 of second clamp member 30 to thereby secure the clamp members one to another at any desired preselected lateral positions of the clamp members. Once the sternal halves SH1 and SH2 have been closed in this way and the clamp members have been rigidly united, the surgical tool 80 is removed by rotating second handle arm 84 downwards and away from first handle arm 82. The surrounding muscle, tissue, and the like may thereafter be closed using conventional sutures, surgical staples or the like. It will be appreciated that a plurality of opposed clamp members 10, 30 can be used to close a severed sternum, if required. Preferably, as noted above, a surgeon will use between three to five pairs of opposed clamp members 10, 30 to secure the sternum. If there is a need to remove the sternal closure device 8, detachment means are provided as described above to permit the clamp members 10, 30 to be separated laterally away from one another.

Figure 7:
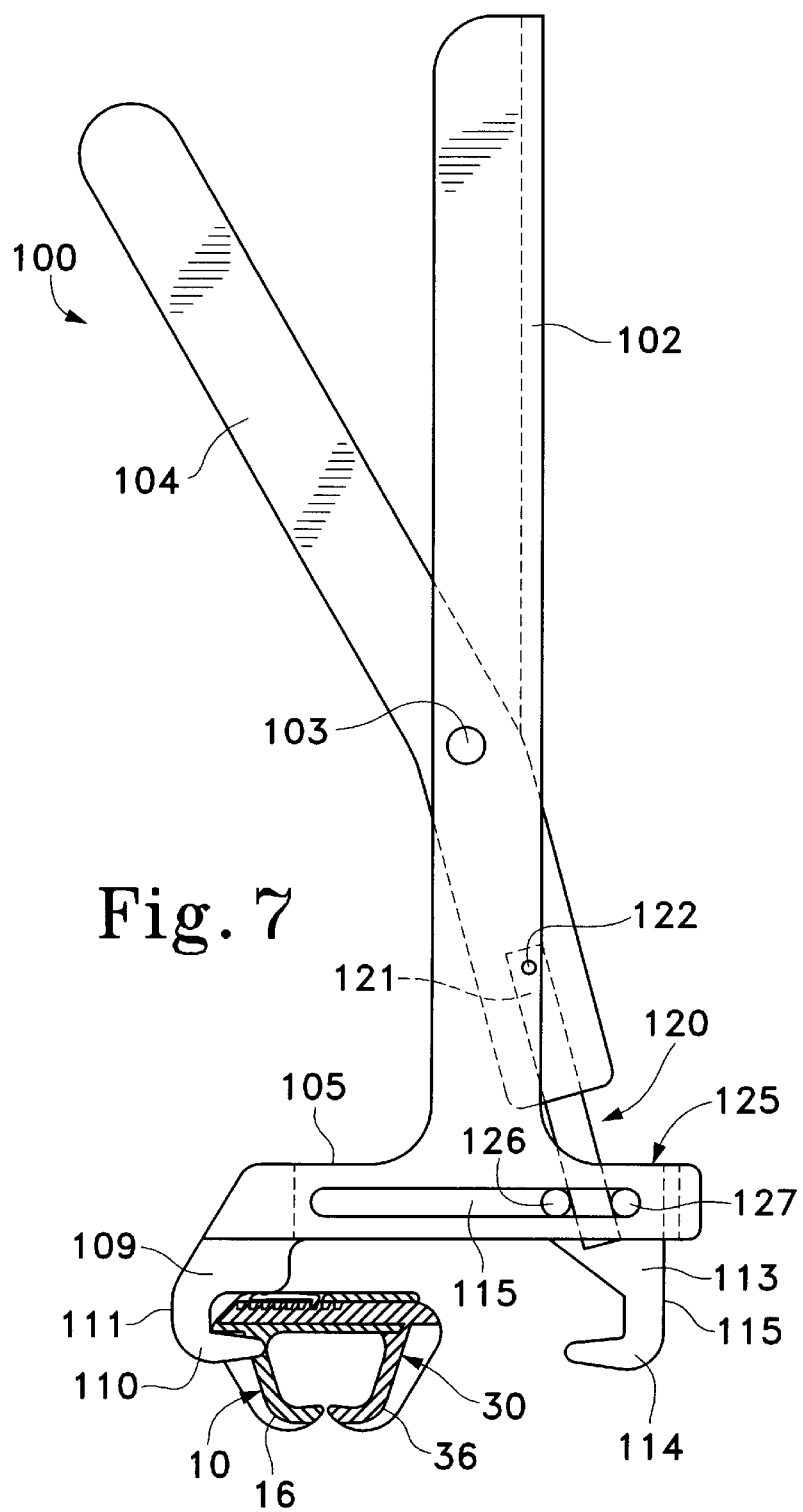
FIG. 7 is a side view of an alternative embodiment of a surgical tool for laterally urging together the opposed clamp members of the present invention.
Figure 7B:
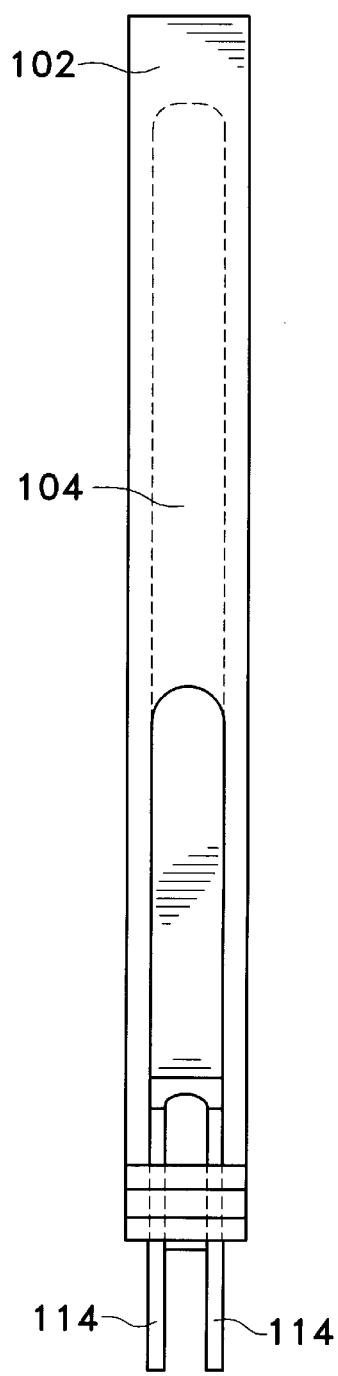
FIG. 7B is a plan view of the surgical tool of FIG. 7.
Figure 7A:
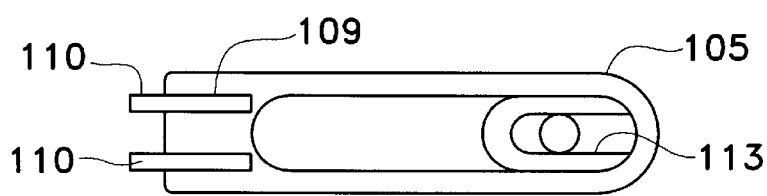
FIG. 7A is a bottom view of the surgical tool of FIG. 7.

FIGS. 7, 7A, and 7B show an alternative embodiment of a surgical tensioning tool for laterally urging together the opposed clamp members 10, 30 during the reapproximation procedure. The surgical tool of this alternative embodiment is configured to be actuated substantially on-axis to the sternal closure device 8 rather than off-axis as is the surgical tool of FIG. 5. Referring to FIG. 7, the tensioning tool is generally indicated by the reference numeral 100. Similar to the surgical tool 80 of FIG. 5, tensioning tool 100 includes a first handle arm 102 and an actuator mechanism which comprises a second handle arm 104 which is pivotally coupled to first handle arm 102 via a coupling pin member 103. However, unlike the tensioning tool 80 of FIG. 5, the first handle arm 102 of this embodiment is oriented substantially perpendicular to an axial centerline of the assembled sternal closure device 8. First handle arm 102 includes a base portion 105 which is rigidly coupled to handle arm 102 at the lower end of the handle arm 102. Base portion 105 has a generally rectangular configuration. A first grasping member 109 is fixedly connected to a lower surface of base portion 105 of first handle arm 102 at one end of the base portion 105.

As best seen in FIG. 7A, first grasping member 109 includes a pair of support rail flanges 110 which are sized and dimensioned to be positioned about opposite sides of the respective engagement leg 16 of one of the opposed clamp members 10. In this way, the lower surface of the bottom side of body portion 12 of clamp member 10, which has a greater width than engagement leg 16, rests against the upper surface of rail flanges 110, as most clearly seen in FIG. 7. Grasping member 109 also includes a rear abutment surface 111 which is adapted to engage and contact the rear outer surface of engagement leg 16. Thus, first clamp member 10 can be securely held in place and laterally supported within the grasping member 109 during the reapproximation procedure. Base portion 105 also includes an axial slot 115 which extends along and through a substantial length of the broad longitudinal sides of base portion 105. Slot 115 is sized and dimensioned to slidably receive the pin members 126, 127 of a carriage assembly 125, as described in greater detail below. A substantial portion of the material of the lower surface of base portion 105 is removed to allow carriage assembly 125 to move laterally along the axial length of the base portion 105 in operation of the device 100, as will also be described below.

The tensioning tool 100 further includes a second grasping member 113 which is moveable laterally in a horizontal plane relative to first grasping member 109. Similar to first grasping member 109, second grasping member 113 includes a pair of support rail flanges 114 (see FIG. 7B) which are sized and dimensioned to engage about and laterally support the opposite sides of the respective engagement leg 36 of the other opposed clamp member 30. Second grasping member 113 also includes a rear abutment surface 115 which is adapted to engage and contact the rear outer surface of engagement leg 36 of clamp member 30. In this way, the other clamp member 30 can be securely held in place within the second grasping member 113 during the reapproximation procedure. A link mechanism 120 is provided which mechanically couples the second grasping member 113 to the pivotal second handle arm 104. Link mechanism 120 includes a rod 121 which is fixedly coupled to the second handle arm 104 at one end of the rod, and movably coupled to the carriage assembly 125 at the other end of the rod 121. Specifically, rod 121 is fixedly connected to the lower portion of second handle arm 104 via a push pin 122 at one end of the rod. The other end of rod 121 is free and sits within a generally rectangular space defined between front and rear carriage pin members 126, 127, respectively, which are rigidly carried by carriage assembly 125. Second grasping member 113 is fixedly connected to carriage assembly 125 at a lower surface of the carriage assembly. Pin members 126, 127 are free to move together within the slot 115 defined within base portion 105 of first handle arm 102.

In operation of the device of FIG. 7, during the reapproximation procedure, the surgeon will position the grasping members 109, 113 of surgical tool 100 about the opposite sides of respective engagement legs 16, 36 of the clamp members 10, 30. The surgeon can then rotate second handle arm 104 upwards towards first handle arm 102 to force rod 121 to move radially laterally and contact and engage the front pin member 126 carried by carriage assembly 125. This will cause carriage assembly 125 to move laterally in a horizontal plane along the axial length of slot 115 of base portion 105 to thereby move clamp member 30 laterally towards first clamp member 10. This will force the ratchet tooth 52 of first clamp member 10 to move in and out of selective engagement with adjacent grooves 72 between ratchet teeth 70 of second clamp member 30 to thereby secure the clamp members to one another at any desired preselected lateral position of the clamp members. Once the sternal halves SH1 and SH2 have been closed in this way and the clamp members have been rigidly united, the surgical tool 100 is removed by rotating second handle arm 104 downwards and away from first handle arm 102. This will cause rod 121 to contact and engage the rear pin member 127 to force carriage assembly 125 and second grasping member 113 connected thereto to move laterally away from first grasping member 109.

Figure 8:
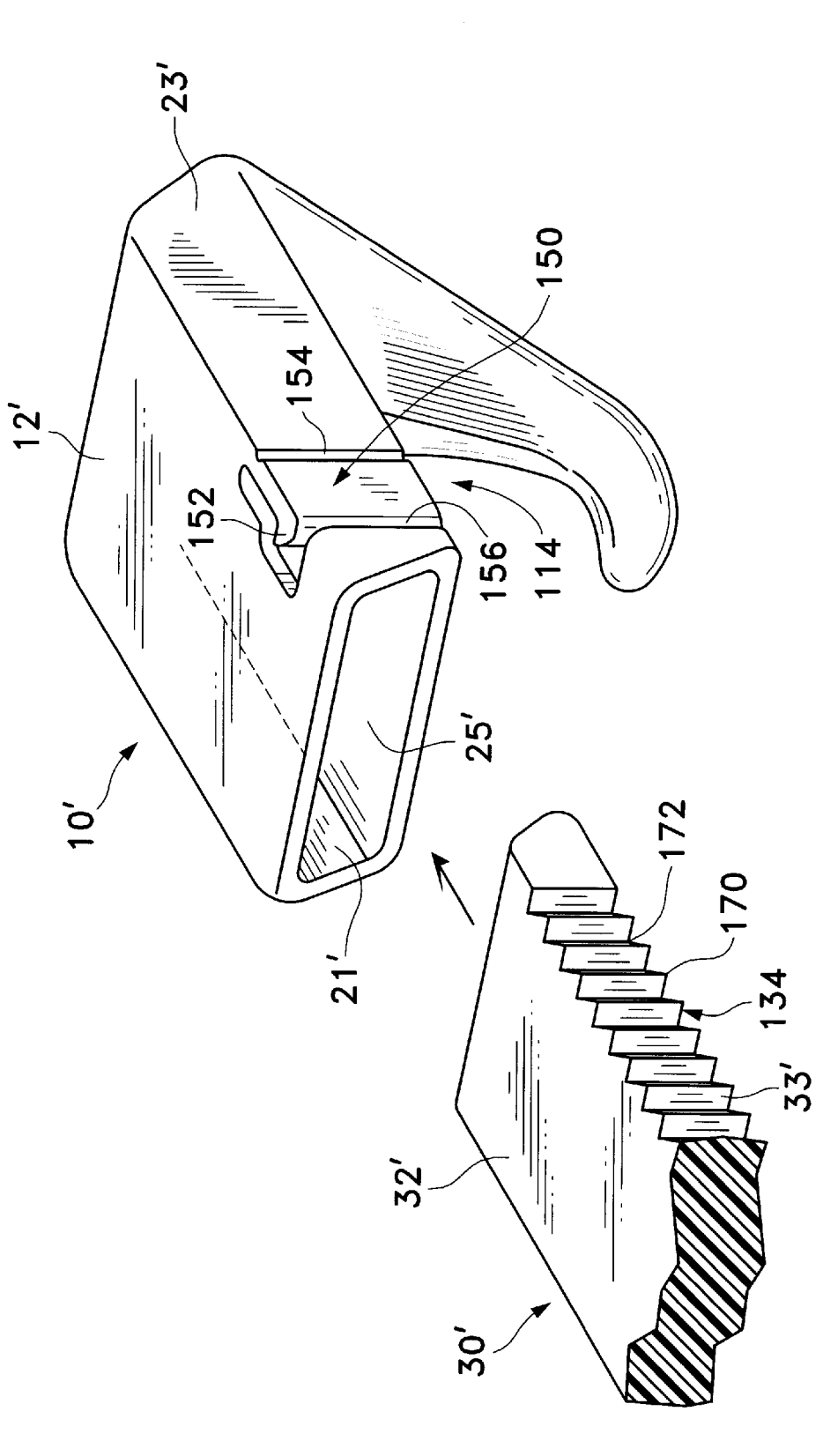
FIG. 8 is a perspective of another embodiment of the invention generally showing the sternal closure device of FIG. 1 with another locking mechanism.
Figure 9:
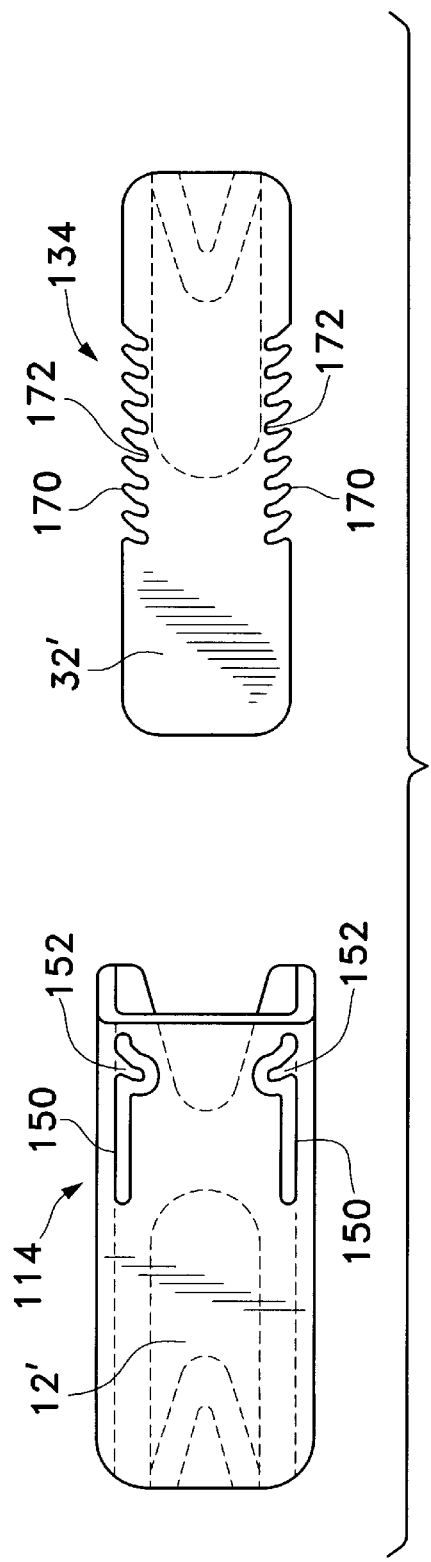
FIG. 9 is a top view of another embodiment of the invention generally showing the sternal closure device of FIG. 1 with another locking mechanism.
Figure 9A:
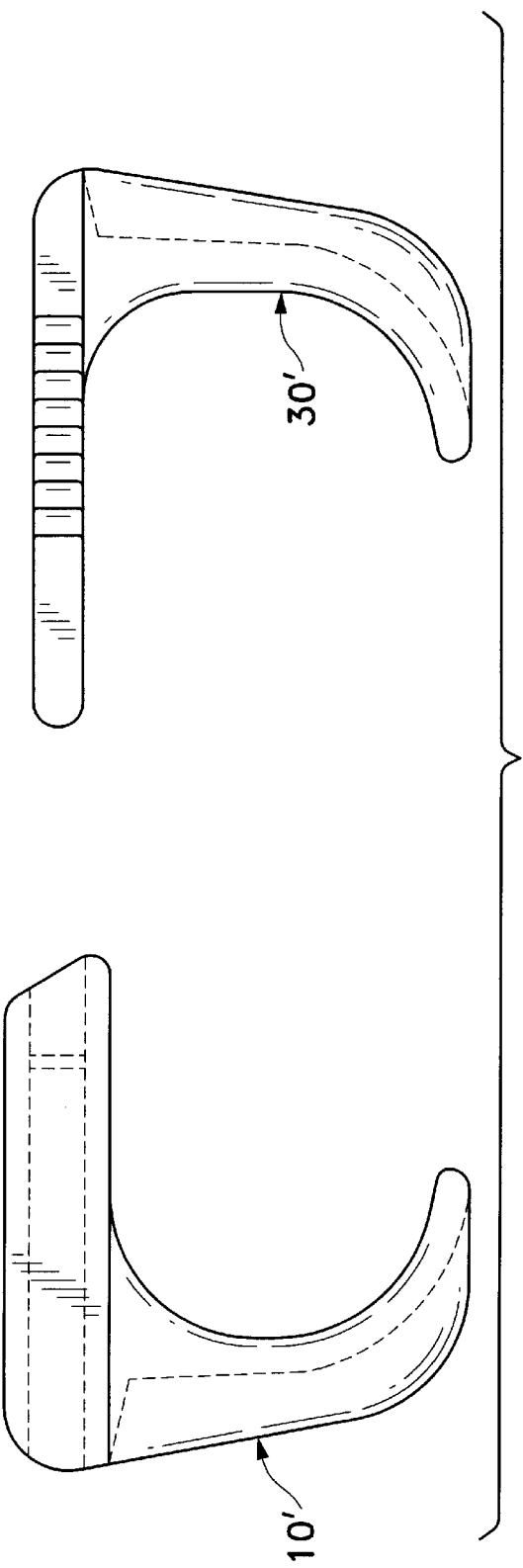
FIG. 9A is a side view of the closure device of FIG. 9.

FIGS. 8 and 9 show alternative embodiments of a locking mechanism for detachably securing modified opposed clamp members 10', 30' to one another. The sternal clamp members 10' and 30' of FIGS. 8 and 9 are substantially structurally identical to the clamp members 10, 30 described above with respect to FIGS. 1–6, except that the locking mechanism is different as will be described below. As shown in FIG. 8, the body portion 12' of first clamp member 10' includes a lock member 114 which includes at least one ratchet pawl 150 integrally connected to longitudinal side 23' of the body portion at rear edge 154 of the pawl. As seen in FIG. 9, lock member 114 can optionally include two ratchet pawls 150.

Rear edge 154 is slightly radiused inwards to allow ratchet pawl 150 to be more easily biased laterally away and transverse to longitudinal side 23'. Ratchet pawl 150 includes at least one ratchet tooth 152 at the opposite end of the ratchet pawl 150 which extends inwardly within recess 25' and faces towards opposite longitudinal side 21'.

The second clamp member 30' includes a catch member 134 comprising at least one set of a plurality of ratchet teeth 170 which extend along and are integral with longitudinal side 33' of body portion 32'. As seen in FIG. 9, catch member 134 can also include two sets of ratchet teeth 170. Ratchet teeth 170 define a plurality of grooves 172 between the teeth which are configured to engage ratchet tooth 152. Where two sets of ratchet teeth are employed as in FIG. 9, the two sets of ratchet teeth 170 are spaced apart such that corresponding grooves 172 between the teeth 170 are in longitudinal registry with one another. As such, when the body portion 32' of second clamp member 30' partially slides within recess 25' of body portion 12' of first clamp member 10', ratchet tooth 152 selectively engages with any one of the grooves 170 (or registered pair of grooves) between ratchet teeth 172 to thereby secure the clamp members one to another at any desired one of a plurality of preselected relative lateral positions of the clamp members. Thus, the lateral dimension between the opposed clamp members can be adjustably selected to fit a particular patient's sternum.

First clamp member 10' further includes detachment means which preferably comprises a small space 156 between ratchet pawl 150 and longitudinal side 21' of body portion 12'. This small space 156 allows a surgeon to quickly and easily release the ratchet pawl 150 from engagement with ratchet teeth 170 by inserting a surgical instrument into the space 156 and biasing the ratchet pawl 150 laterally away from ratchet teeth 170. The radiused rear edge 154 of ratchet pawl 150 facilitates lateral upward movement of the pawl 150 by the surgeon. Thus, if there is any need to remove the device and quickly separate the clamp members from one another, the lock member 114 may be simply disengaged from catch member 134 so that the clamp members 10', 30' can be separated laterally away from one another.

Figure 10:
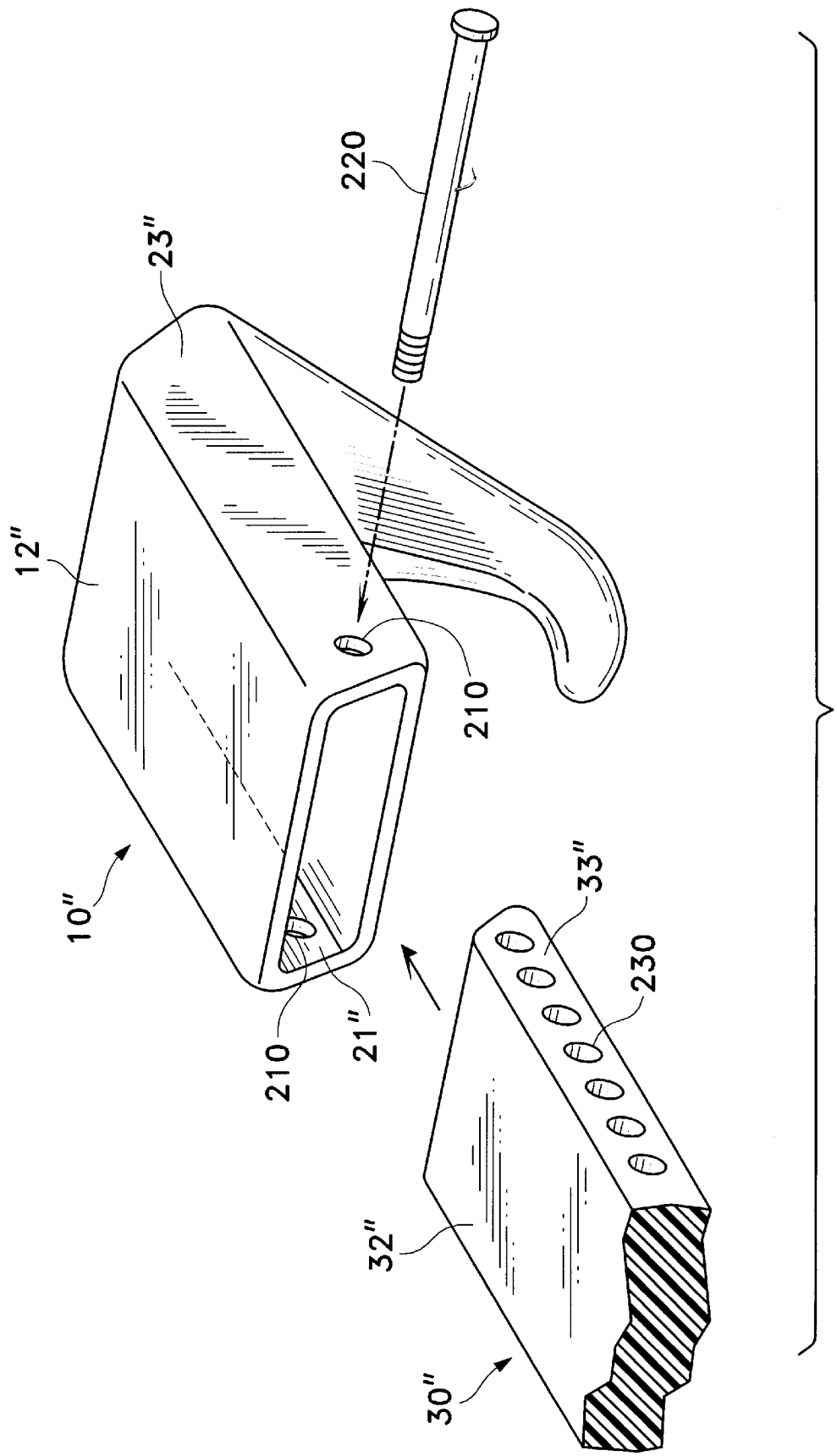
FIG. 10 is a perspective of another embodiment of the invention generally showing the sternal closure device of FIG. 1 with another locking mechanism.

FIG. 10 includes another alternative embodiment of a locking mechanism of the present invention. Again, the modified sternal clamp members 10" and 30" shown therein are substantially structurally identical to the clamp members 10, 30 described above with respect to FIGS. 1–6 except that the locking mechanism is different. As shown in FIG. 10, body portion 12" of clamp member 10" includes at least one threaded through aperture 210 extending between and through longitudinal sides 21" and 23" of body portion 12". Threaded through aperture 210 is configured to permit insertion of a threaded pin 220 therethrough as will be described in greater detail below.

Body portion 32" of second clamp member 30" includes a plurality of longitudinally spaced, axially aligned through apertures 230 between and through longitudinal sides 31", 33" of body portion 32". As can be appreciated, any pair of apertures 230 in body portion 32" may be brought into longitudinal registration with aperture 210 in body portion 12" when body portion 32" is partially received within body portion 12". The locking mechanism further comprises a separate lock member which includes a threaded pin member 220. Pin member 220 is configured to be threadably inserted through any pair of registered aperture pairs 210, 230 to rigidly, but removably, unite the clamp members 10", 30" to one another. To separate the clamp members 10", 30" from one another, threaded pin member 220 may be quickly and easily removed from aperture pairs, 210, 230.

Figure 11:
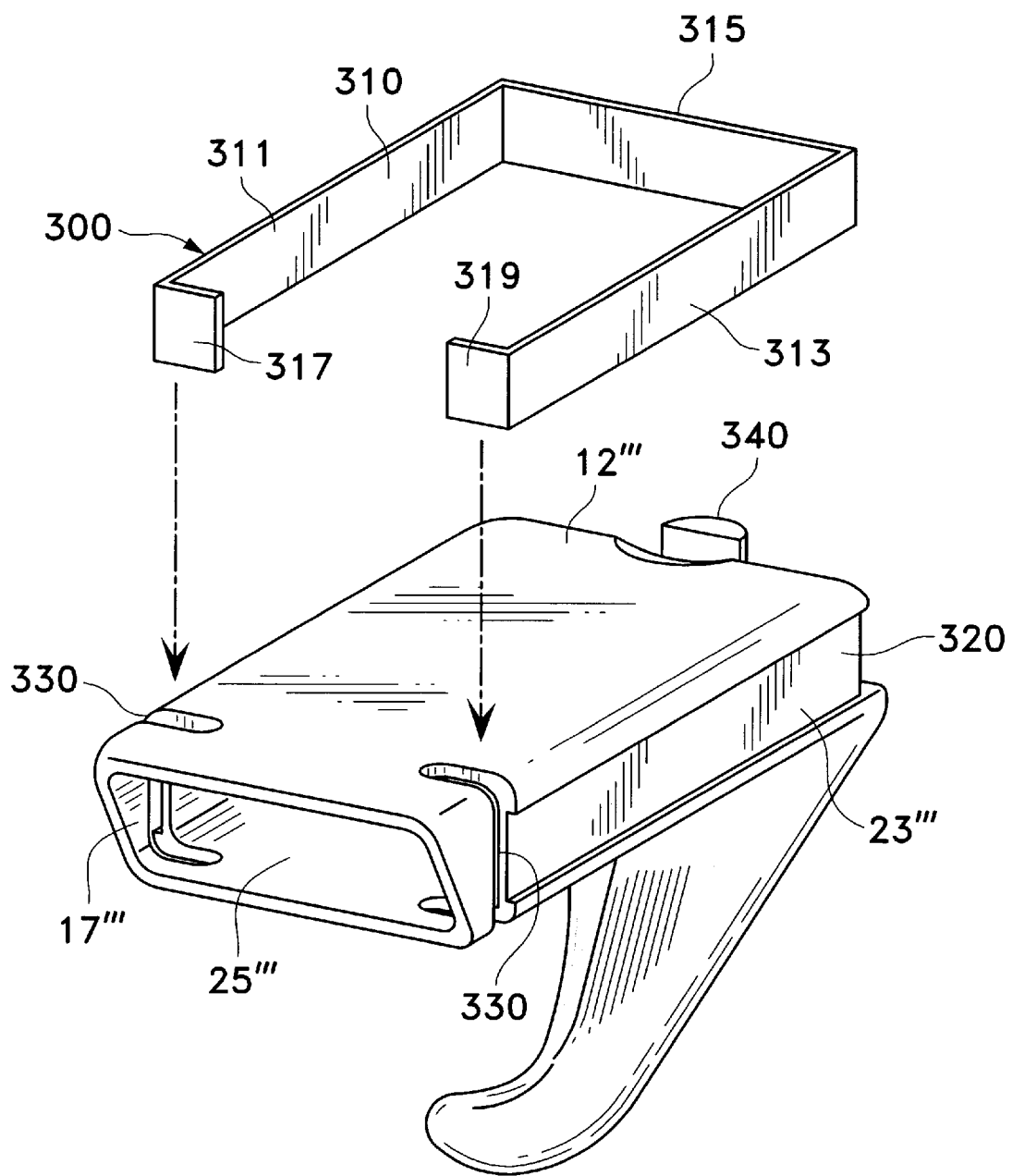
FIG. 11 is a perspective of another embodiment of the invention generally showing the sternal closure device of FIG. 1 with another locking mechanism

FIG. 11 depicts another alternative embodiment of a locking mechanism of the present invention. As above, the modified sternal clamp members 10'" and 30'" shown therein are substantially structurally identical to the clamp members 10, 30 described above with respect to FIGS. 1–6, except that the locking mechanism is different, as will be described below. Similar to the locking mechanism of FIG. 9, the second clamp member (not shown) is provided with two sets of ratchet teeth which are integral with and extend along opposite longitudinal sides of its body portion. As shown in FIG. 11, body portion 12'" of first clamp 10'" member includes a contiguous locking channel 320, or recess, extending along the broad longitudinal sides and the rear side of the body portion. The locking channel 320 terminates on both longitudinal sides of the body portion at respective slots 330 located in the longitudinal sides of the body portion 12'" near the front side 17'" of the body portion. The locking mechanism further includes a separate lock member 300 including a generally U-shaped locking member 310 which is sized to sit squarely within the locking channel 320. Preferably, the locking member 310 is made from surgical grade stainless steel for strength, but any other suitable relatively strong biocompatible material would suffice as would be well-known to the person of ordinary skill in the art. The locking member 310 comprises first and second parallel, longitudinal sides 311, 313 and an integral end side 315 integrally joined to the longitudinal sides. The longitudinal sides 311, 313 of locking member 310 terminate in respective flanges 317, 319 which are configured to fit within slots 330. A rear flange 340 is integrally connected to the rear end of the body portion 12'" and is adapted to bias locking member 310 against locking channel 320 to hold it securely in place.

In use of the device of FIG. 11, with the clamp members positioned about respective sternal halves, the second clamp member is selectively positioned partially within recess 25'" of body portion 12'" at any desired preselected lateral position of the clamp members. This allows the surgeon to selectively adjust the lateral dimension between the clamp members to fit a particular patient's sternum. Once the clamp members are properly positioned and the sternal halves are brought together, locking member 310 is positioned in the locking channel 320 so that flanges 317, 319 sit within slots 330. Flanges 317, 319 engage with a respective pair of aligned grooves between the ratchet teeth carried by the second clamp member to thereby secure the clamp members one to another at the desired relative lateral position of the clamp members. If there is any need to quickly remove the sternal closure device to gain access to the patient's thoracic cavity (such as in a medical emergency), rear flange 340 can be urged laterally away from locking channel 320 with any suitable surgical instrument so that locking member 310 can be removed and the clamp members (and the sternal halves to which they are engaged) can be separated laterally away from one another.

Figure 12:
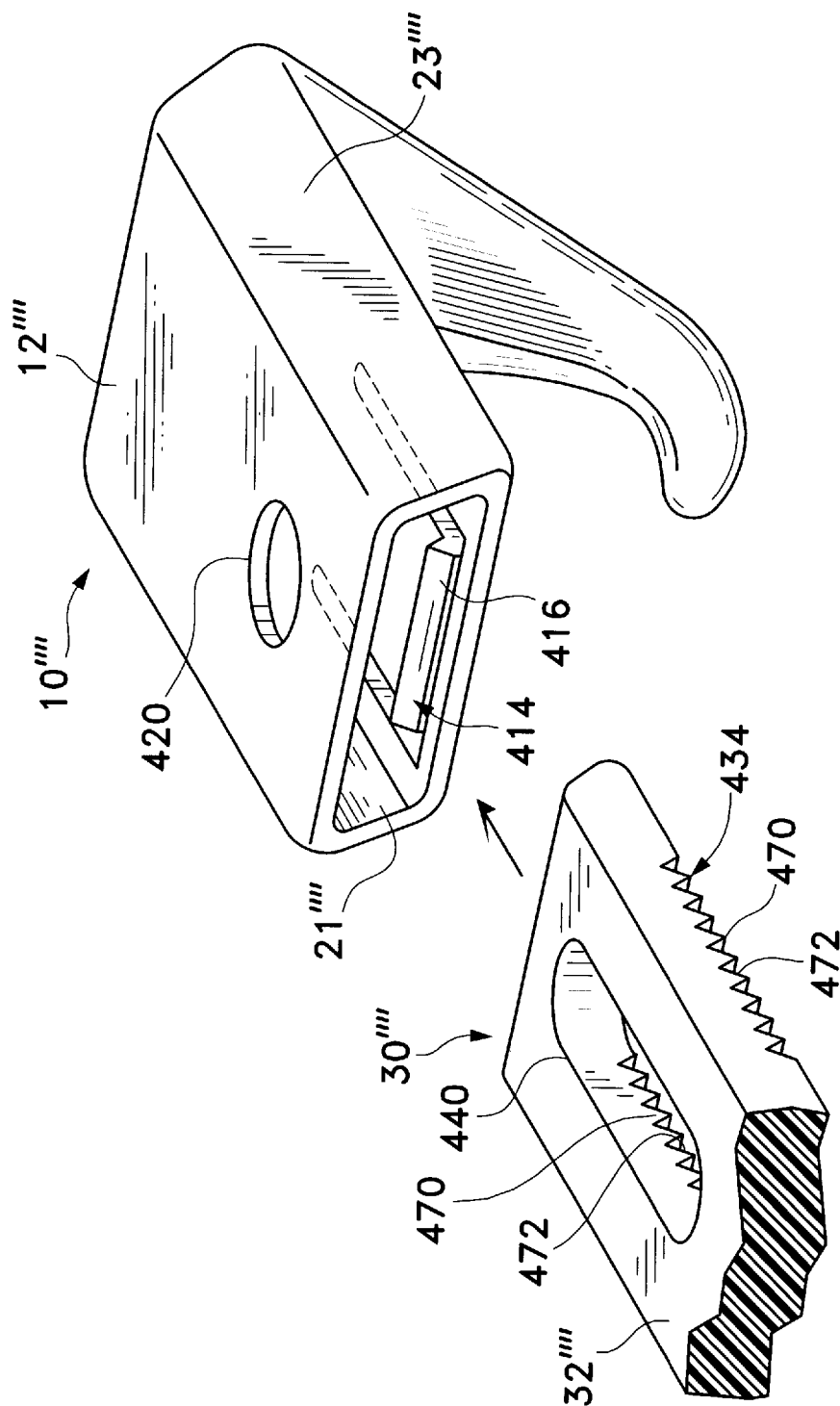
FIG. 12 is a perspective of another embodiment of the invention generally showing the sternal closure device of FIG. 1 with another locking mechanism.

In yet another embodiment of a locking mechanism shown in FIG. 12, the second clamp member 30"" includes a catch member 434 which comprises at least two sets of ratchet teeth 470 which are integral with and extend longitudinally along the lower surface of the body portion 32"" of clamp member 30"". The ratchet teeth 470 each define a plurality of grooves 472 therebetween, and the two sets of ratchet teeth 470 are spaced apart such that each groove 472 is in longitudinal registry with a corresponding groove 472 in the opposed set of ratchet teeth. A ratchet pawl release slot 440 is provided through the top and bottom sides of body portion 32"" between the two sets of ratchet teeth 472 to permit a surgical instrument to be inserted through body portion 32"" to release engagement between the clamp members, as will be described below.

Body portion 12"" of first clamp member 10"" comprises a lock member 414 which is configured to engage catch member 434 carried by second clamp member 30"". Lock member 414 comprises a ratchet pawl 416 which is integral with and extends transverse to the inner surface of the bottom side of body portion 12"" between the longitudinal sides 21"", 23"" of the body portion. Ratchet pawl 416 is configured to selectively engage with any one of a pair of aligned grooves 472 between the two sets of ratchet teeth 470. A pawl release port 420 is provided in the upper surface of body portion 12"" which allows a surgeon to quickly and easily release the ratchet pawl 416 from engagement with ratchet teeth 470 by inserting a surgical instrument into the port 420 and through the pawl release slot 440 to bias the ratchet pawl 416 downwards and out of engagement with the ratchet teeth 470.

Figure 13:
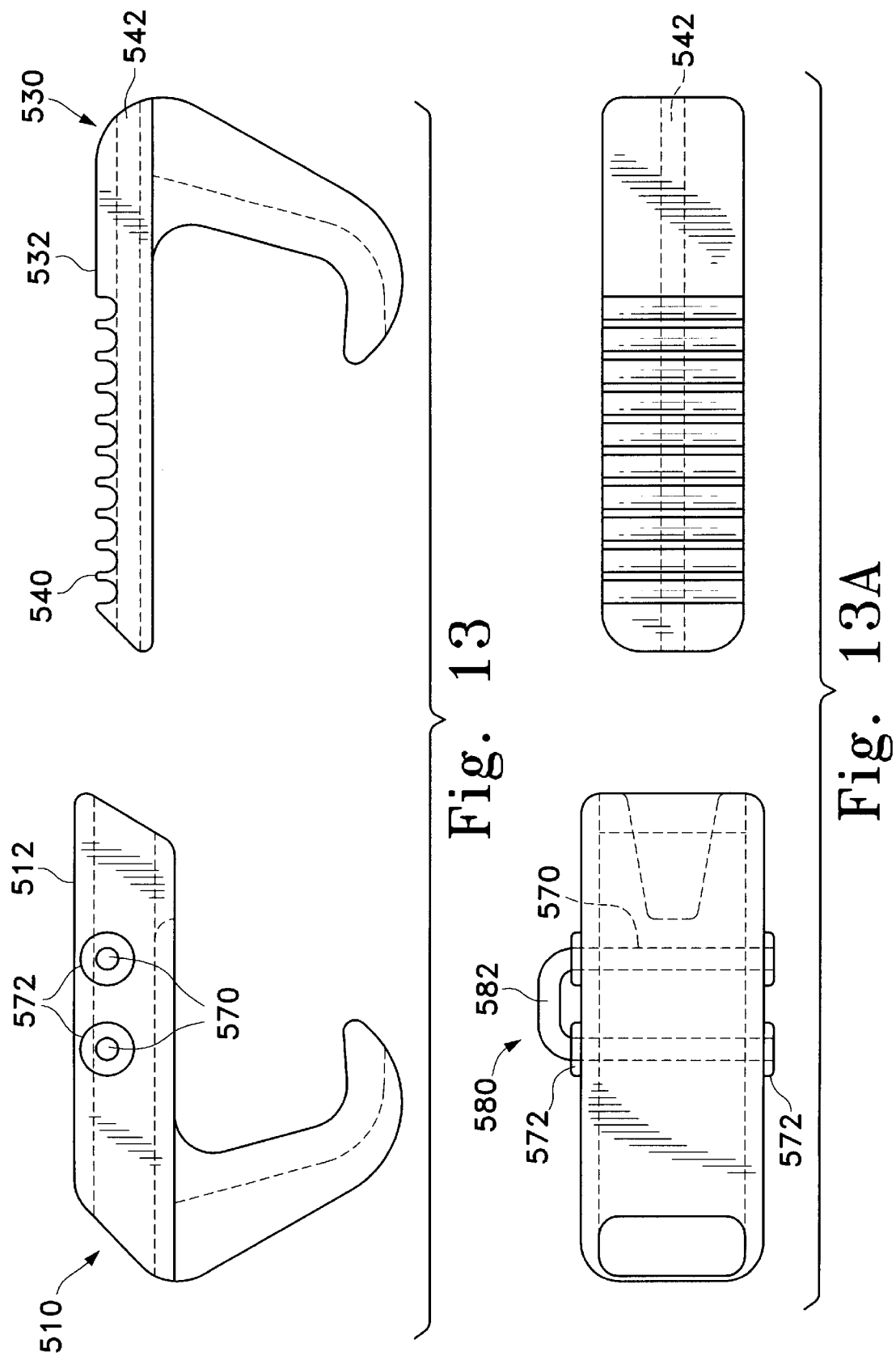
FIG. 13 is side view of another embodiment of the invention generally showing the sternal closure device of FIG. 1 with another locking mechanism.

FIGS. 13 and 13A show a preferred embodiment of a locking mechanism for rigidly and detachably securing the body portion of one opposed clamp member at least partially within the body portion of another clamp member at any one of a plurality of relative lateral positions between the clamp members. In FIG. 13, the body portion 532 of second clamp member 530 is similar to body portion 32" of FIG. 10 except that the through apertures are replaced with a plurality of axially aligned, spaced apart rounded slots 540 which extend along the upper surface of body portion 532. The provision of slots 540 instead of through apertures is advantageous in that the slots 540 provide sufficient space beneath the slots for a stainless steel stiffening rod 542 to be inserted within the interior of body portion 532. Stiffening rod 542 extends along the axial length of body portion 532 and helps to enhance the strength and rigidity of the body portion.

Body portion 512 of the first clamp member 510 includes at least one pair of corresponding through apertures 570 which extend along and through the broad longitudinal sides of the body portion 512. As can be appreciated, any pair of adjacent slots 540 in body portion 532 may be brought into longitudinal registration with apertures 570 in body portion 512 when body portion 532 is partially received within body portion 512. The locking mechanism further comprises a separate lock member 580 which includes a U-shaped, dual-arm pin member 582 as seen inserted into the clamps in FIG. 13A. Pin member 582 is configured to be inserted through apertures 570 and across any pair of adjacent slots 540 to rigidly, but removably, unite the clamp members 510, 530 to one another. As best seen in FIG. 13A, a small annular button member 572 is provided around apertures 570 on both external surfaces of the longitudinal sides of body portion 512 to provide a small clearance space between the U-shaped distal end portion of pin member 582 and the external surface of the longitudinal sides of body portion 512. This clearance provides sufficient room for a surgeon to grasp the U-shaped distal end portion of pin member 582 and easily remove it from engagement with the clamp members 510, 530 if it is necessary to quickly separate the clamp members from one another.

A retaining member may be added to prevent the pin member 582 from falling out of the body portion 512. The retaining member may comprise openings 533 extending through one or both legs of the pin member 582 for receiving a suture 535. The legs of the pin member 582 may also be sized to provide an interference fit between the pin member and apertures 570. It is to be understood that other types of retaining members may be used.

Figure 14:
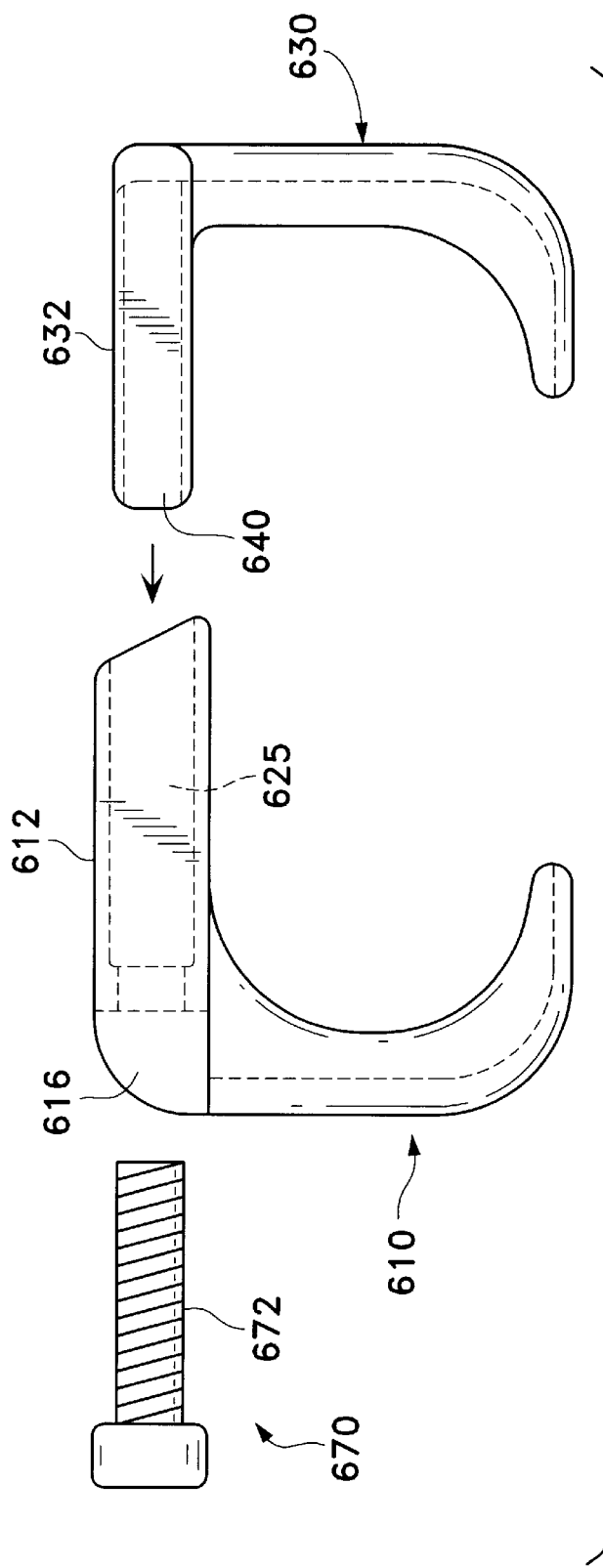
FIG. 14 is a side view of another embodiment of the invention generally showing the sternal closure device of FIG. 1 with another locking mechanism.
Figure 14A:
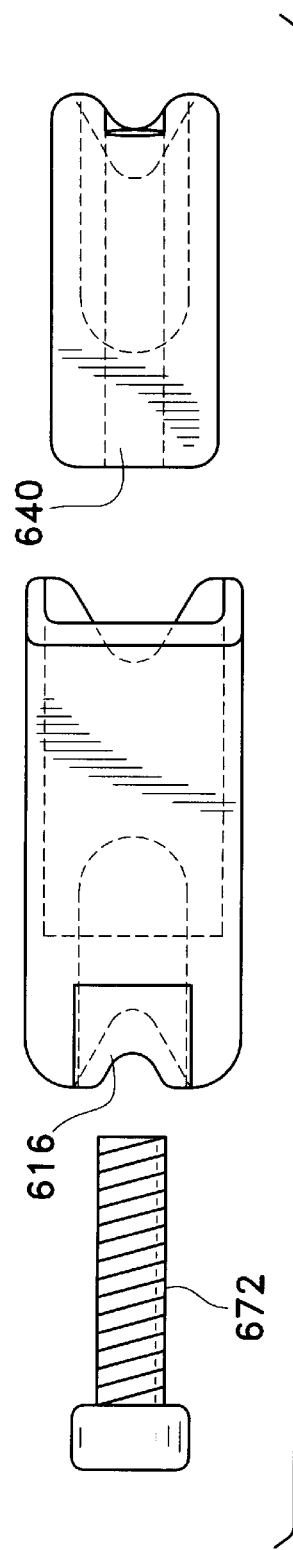
FIG. 14A is a top view of the closure device of FIG. 14.

FIGS. 14 and 14A illustrate another alternative embodiment of a locking mechanism for detachably securing the body portion of the second clamp member partially within a recess provided in the body portion of the first clamp member. In this embodiment, the second clamp member 630 is securely held in place within the recess 625 provided in the body portion 612 of the first clamp member 610 by inserting a separate lock member 670 comprising a threaded socket head cap screw 672 into a countersunk hole 616 provided in the rear surface of the first clamp member 610. The cap screw 672 is configured to be threadably received within a threaded aperture 640 in body portion 632 of second clamp member 630 which extends at least partially along the axial length of body portion 632 from the front end of the body portion towards its rear end. A torque wrench or other appropriate torque-limiting device (not shown) can be used by the surgeon to prevent stripping of the socket head cap screw 672 as the surgeon adjusts the lateral dimension between the clamp members 610, 630 to secure the device about the reapproximated sternum. The socket head pin screw 672 can also be easily removed to quickly and easily separate the clamp members 610, 630 from one another, if necessary.

Figure 15:
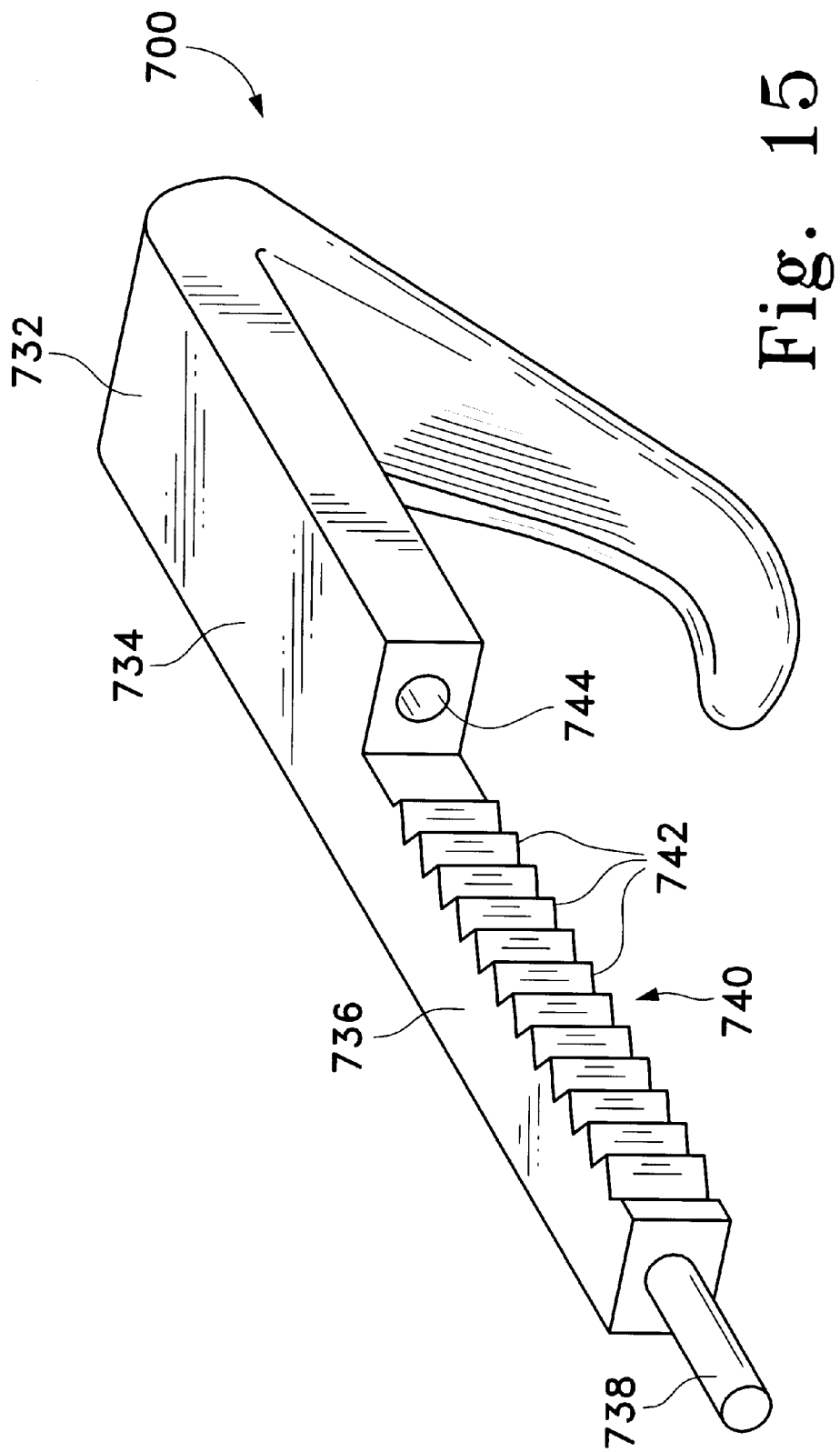
FIG. 15 is a perspective of an alternative embodiment of the sternal closure device of FIG. 1 showing one of a pair of identical clamp members in a disassembled state which is adapted to mate with another structurally identical clamp member in a side-by-side interlocking relationship.

FIG. 15 illustrates an alternative embodiment of the sternal closure device of FIG. 1 in which the opposed clamp members are not configured to be slidably received one partially within the other. Instead, the clamp members 700 of this embodiment, which are structurally identical to each other, mate and interlock with one another in a side-by-side relationship. One of the advantages of the embodiment of FIG. 15 is that the device, in its assembled state, preferably provides a smaller profile within the thoracic cavity than the device of FIG. 1 because the clamp members do not overlap one another. Another advantage of this particular embodiment is that it is relatively simple to manufacture because it only requires a single mold to fabricate the two parts of the device.

Referring to FIG. 15, one of the two identical clamp members 700 is provided which is identical in all respects to the clamp member 30 described above with reference to FIG. 1 except that the elongate planar body portion 732 is different. Body portion 732 of clamp member 700 includes two integral parts, an elongated portion 734 having a width and a planar arm portion 736 which is integrally connected to one end of spanning portion 734 and which has approximately one half the width of planar spanning portion 734. Planar arm portion 736 includes a guide pin member 738 connected to the end of arm portion 736 and an integral lock/catch member 740 comprising a plurality of barbs, or ratchet teeth, 742 which extend along the inner longitudinal surface of arm portion 736. A corresponding hole 744 is provided in the end of spanning portion 734 adjacent arm portion 736 which is sized and dimensioned to receive an identical guide pin member 738 (not shown) of a structurally identical opposed clamp member 700 (not shown). The elongated portion of the second clamp member is adapted to engage the elongated portion of the first clamp member 700 without substantially overlapping the first clamp member.

In operation, the two identical opposed clamp members 700 are brought together in a side-by-side relationship such that corresponding sets of ratchet teeth 742 selectively engage with one another at any one of a plurality of relative lateral positions between the clamp members. Guide pin member 738 has a sufficient length such that corresponding pin members 738 slide at least partially within opposed, corresponding holes 744 provided within spanning portion 734 of the opposed clamp members 700 when the clamp members are positioned about respective sternal halves of a patient's severed sternum. Guide pin members 738 ensure that the clamp members 700 are longitudinally aligned and rigidly interlocked with one another. If necessary, to separate the clamp members from one another, a surgeon can wedge a thin shim-like tool into the small space between the arm portions 736 of the clamp members to bias the ratchet teeth 742 out of engagement with one another. If necessary, pin members 738 can be made sufficiently thin such that they can be made to break when the shim is wedged into the space between arm portions 736 and rotated to apply a sufficient shear load on the pin members 738. This will facilitate lateral separation of the clamp members 700 from one another.

FIG. 16 illustrates an alternative embodiment of the sternal closure device of FIG. 15 in which a separate lock member is used to removably secure the body portions of identical opposed clamp members to one another in a side-by-side relationship. The clamp member 800 of FIG. 16 is similar in all respects to the clamp member 700 of FIG. 15 except that the ratchet teeth are replaced with a plurality of axially aligned threaded through apertures 842. Apertures 842 extend along opposed sides of arm portion 836 of body portion 832 of the clamp member 800. The series of axially aligned threaded through apertures 842 are configured to be in longitudinal registration with a corresponding plurality of axially aligned threaded through apertures extending along opposed sides of an arm portion of an identically configured clamp member 800 (not shown). In this way, one or more pairs of registered through apertures are defined between the body portions of identical clamp members. At least one separate lock member 850 is provided which is configured to be threadably received by a respective pair of registered through apertures to rigidly, but removably, unite the clamp members 800 to one another. The lock member can comprise one or more threaded cap screws as shown, a U-shaped pin member (not shown) (in which case holes 842 would not be threaded), or any other type of locking pin member as would be obvious to the person of ordinary skill in the art. Planar arm portion 836 may optionally include a guide pin member 838 connected to the end of arm portion 836 which is configured to be received within a corresponding hole 844 provided in the end of a spanning portion of an identical clamp member 800 (not shown).

It should be understood that while the above is a complete description of the preferred embodiments of the invention, various alternatives, modifications and equivalents may be used. Therefore, the above description should not be taken as limiting the scope of the invention which is defined by the following claims.

What is claimed is:

1. A sternal closure device comprising first and second clamps which are adapted for substantially surrounding an adult patient's sternum and each having an integral end portion, said first clamp having a generally tubular portion and said second clamp having a portion slidably receivable in said tubular portion, wherein said integral end portion substantially extends towards said other end portion when said first clamp is slidably received in said second clamp, and said second clamp is releasably retained within said first clamp.

2. The device of claim 1 wherein each clamp has a generally J-shaped portion.

3. The device of claim 1 wherein each clamp has a generally C-shaped portion.

4. The device of claim 1 wherein at least one of said clamps includes a sternum engaging surface, said sternum engaging surface including a plurality of ribs.

5. The device of claim 1 wherein at least one of said clamps includes a sternum engaging surface, said sternum engaging surface including a plurality of teeth.

6. The device of claim 1 wherein at least one of said clamps includes a sternum engaging surface, said sternum engaging surface including a plurality of protrusions.

7. The device of claim 1 wherein said lock comprises a locking member operatively coupled to one of said clamps and a receiving member operatively coupled to the other one of said clamps, said receiving member adapted for lockingly receiving the locking member.

8. The device of claim 1 further comprising a lock which forms a permanent connection between the first and second clamps.

9. The device of claim 1 wherein said tubular portion is rectangular in transverse cross-section.

10. The sternal closure device of claim 1 where said first and second clamps are sized and dimensioned to engage opposite sides of a patient's severed sternum.

11. A sternal closure device comprising a first and a second clamp, said first clamp having a generally tubular portion and said second clamp having a portion that is slidably receivable in said tubular portion, and a lock configured to retain said second clamp within said first clamp wherein at least one of said clamps includes a sternum engaging surface formed of a surface tension enhancing material.

12. A surgical device for reapproximating the sternal halves of a patient's severed sternum following a partial or median sternotomy comprising:

a first clamp member including an elongate body portion and a generally J-shaped engagement leg extending from said body portion, said body portion forming a recess;

a second clamp member including an elongate body portion and configured to be at least partially received within said recess, said second clamp member further comprising a generally J-shaped engagement leg extending from said body portion, wherein said second clamp engagement leg has an integral portion which extends towards an integral portion of said first clamp engagement leg when said second clamp member is received within said recess; and means for releasably securing said body portion of said first clamp member to said body portion of said second clamp member.

13. The surgical device of claim 12 wherein said clamp members are made from biocompatible material.

14. The surgical device of claim 13 wherein said biocompatible material comprises a radiolucent material.

15. The surgical device of claim 12 wherein said engagement legs of said first and second clamp members each include a main spine portion.

16. The surgical device of claim 15 wherein said main spine portion is integrally connected to a generally planar foot portion.

17. The surgical device of claim 16 wherein said foot portion is configured to be spaced apart from a posterior surface of a respective sternal half.

18. The surgical device of claim 15 wherein said spine portion is integrally connected to the body portion of the respective first and second clamp members.

19. The surgical device of claim 15 wherein said spine portion is generally curved.

20. The surgical device of claim 15 wherein said spine portion is generally straight and extends inwardly at an angle of between about 45 and 90 degrees from said body portion relative to a central longitudinal axis of the body portion.

21. The surgical device of claim 12 wherein said securing means comprises:
- at least one lock member connected to a top side of said body portion of said first clamp member including a ratchet pawl having at least one inwardly directed ratchet tooth;
- at least one corresponding catch member connected to an upper surface of said body portion of said second clamp member including a plurality of ratchet teeth which define a plurality of grooves therebetween; and
- wherein said ratchet tooth is configured to selectively engage with any one of said plurality of grooves defined between said plurality of ratchet teeth when said body portion of said second clamp member is partially received within the recess of the body portion of the first clamp member to thereby secure the first and second clamp members one to another at any one of a plurality of preselected lateral positions of the clamp members.

22. The surgical device of claim 12 wherein said securing means comprises:
- at least one lock member connected to a longitudinal side of said body portion of said first clamp member comprising a ratchet pawl including at least one inwardly-directed ratchet tooth;
- at least one corresponding catch member connected to a longitudinal side of said body portion of said second clamp member comprising a plurality of ratchet teeth defining a plurality of grooves therebetween; and
- wherein said at least one ratchet tooth is configured to selectively engage with any one of said plurality of grooves when said body portion of said second clamp member is partially received within the recess on the body portion of the first clamp member to thereby secure the first and second clamp members one to another at any one of a plurality of preselected lateral positions of the clamp members.

23. The surgical device of claim 22 further including detachment means for releasing said lock member from engagement with said catch member to thereby allow said first and second clamp members to be laterally separated from one another.

24. The surgical device of claim 12 wherein said securing means comprises:
- at least one threaded through aperture through opposite longitudinal sides of said body portion of said first clamp member;
- a catch member connected to said body portion of said second clamp member which comprises a plurality of axially aligned through apertures through opposite longitudinal sides of said body portion which are configured to be selectively in registry with said at least one threaded through aperture in the longitudinal sides of the body portion of the first clamp member to thereby define at least one pair of registered through apertures between the body portions of the first and second clamp members; and
- a separate lock member comprising at least one threaded pin member which is configured to be threadably received by said at least one pair of registered through apertures to rigidly, but removably, unite said clamp members one to another at any one of a plurality of preselected lateral positions of the clamp members.

25. The surgical device of claim 12 wherein said securing means comprises:
- a lock member connected to a bottom side of said body portion of said first clamp member comprising a ratchet pawl having at least one inwardly-directed ratchet tooth;
- a corresponding catch member connected to a lower surface of said body portion of said second clamp member comprising at least one set of a plurality of ratchet teeth defining a plurality of grooves therebetween; and
- wherein said at least one ratchet tooth of said ratchet pawl is configured to selectively engage with any one said grooves between said at least one set of ratchet teeth when said body portion of said second clamp member is partially received within the recess of the body portion of the first clamp member to thereby secure the first and second clamp members one to another at any one of a plurality of predetermined lateral positions of the clamp members.

26. The surgical device of claim 12 wherein said securing means comprises:
- a separate lock member comprising a threaded cap screw;
- a threaded aperture extending from a front end of said body portion of said second clamp member through at least a portion of an axial length of the body portion which is configured to threadably receive said cap screw; and
- a guide hole in a rear end of said body portion of said first clamp member which is configured to permit insertion of said cap screw through said guide hole and into said recess to thereby threadably engage said threaded aperture when said body portion of said second clamp member is partially received within the recess in the body portion of the first clamp member.

27. A surgical device for reapproximating the sternal halves of a patient's severed sternum following a partial or median sternotomy comprising:
- a first clamp member including an elongate body port on and a generally C-shaped engagement leg extending from said body portion, said body portion forming a recess;
- a second clamp member including an elongate body portion and configured to be at least partially received within said recess, said second clamp member further comprising a generally C-shaped engagement leg extending from said body portion, wherein said second clamp engagement leg has an integral portion which extends towards an integral portion of said first clamp engagement leg when said second clamp member is received within said recess; and
- means for releasably securing said body portion of said first clamp member to said body portion of said second clamp member.

28. A surgical device for reapproximating the sternal halves of a patient's severed sternum following a partial or median sternotomy comprising:
- a first clamp member including an elongate body portion adapted to engage one respective sternal half of the patient's severed sternum and an engagement leg extending from said body portion, said body portion forming a recess;
- a second clamp member including an elongate body portion adapted to engage the other respective sternal half of the patient's severed sternum and configured to be at least partially received within said recess, said second clamp member further comprising an engagement leg extending from said body portion;
- wherein said engagement legs of said first and second clamp members each include a main spine portion being generally straight and extending inwardly at an angle of between about 70 and 80 degrees from said body portion relative to a central longitudinal axis of the body portion; and means for securing said body portion of said first clamp member to said body portion of said second clamp member.

29. A surgical device for reapproximating the sternal halves of a patient's severed sternum following a partial or median sternotomy comprising:

a first clamp member including an elongate body portion adapted to engage one respective sternal half of the patient's severed sternum and an engagement leg extending from said body portion, said body portion forming a recess;

a second clamp member including an elongate body portion adapted to engage the other respective sternal half of the patient's severed sternum and configured to be at least partially received within said recess, said second clamp member further comprising an engagement leg extending from said body portion;

wherein said engagement legs of said first and second clamp members each include a main spine portion being generally straight and extending inwardly at an angle of about 75 degrees from said body portion relative to a central longitudinal axis of the body portion; and means for securing said body portion of said first clamp member to said body portion of said second clamp member.

30. A surgical device for reapproximating the sternal halves of a patient's severed sternum following a partial or median sternotomy comprising:

a first clamp member including an elongate body portion and an engagement leg extending from said body portion which includes a main spine portion having an inner sternal engagement surface, said body portion forming a recess;

a second clamp member including an elongate body portion and configured to be at least partially received within said recess, said second clamp member further comprising an engagement leg extending from said body port on which includes a main spine portion having an inner sternal engagement surface, wherein said second clamp engagement leg has an integral portion which extends towards an integral portion of said first clamp engagement leg when said second clamp member is received within said recess; and means for releasably securing said body portion of said first clamp member to said body portion of said second clamp member.

31. The surgical device of claim 30 wherein said inner sternal engagement surface includes a plurality of vertically aligned ribs which are adapted to enhance a gripping force of said sternal engagement surface.

32. The surgical device of claim 30 wherein said inner sternal engagement surface includes a plurality of vertically aligned teeth defining grooves therebetween.

33. The surgical device of claim 30 wherein said inner sternal engagement surface includes a plurality of protrusions which are adapted to enhance a gripping force of said sternal engagement surface.

34. A surgical device for reapproximating the sternal halves of a patient's severed sternum following a partial or median sternotomy comprising:

a first clamp member including an elongate body portion adapted to engage one respective sternal half of the patient's severed sternum and an engagement leg extending from said body portion, said body portion forming a recess;

a second clamp member including an elongate body portion adapted to engage the other respective sternal half of the patient's severed sternum and configured to be at least partially received within said recess, said second clamp member further comprising an engagement leg extending from said body portion;

wherein said engagement legs of said first and second clamp members each include a main spine portion which includes an inner sternal engagement surface including an outer coating composed of a surface tension-enhancing material; and means for securing said body portion of said first clamp member to said body portion of said second clamp member.

35. A surgical device for reapproximating the sternal halves of a patient's severed sternum following a partial or median sternotomy comprising:

a first clamp member including an elongate body portion adapted to engage one respective sternal half of the patient's severed sternum and an engagement leg extending from said body portion, said body portion forming a recess;

a second clamp member including an elongate body portion adapted to engage the other respective sternal half of the patient's severed sternum and configured to be at least partially received within said recess, said second clamp member further comprising an engagement leg extending from said body portion;

where said engagement legs of said first and second clamp members each include a main spine portion which includes an inner sternal engagement surface including an outer sleeve composed of a surface tension-enhancing material; and means for securing said body portion of said first clamp member to said body portion of said second clamp member.

36. The surgical device of claim 35 wherein said surface tension-enhancing material comprises silicone material.

37. A surgical device for reapproximating the sternal halves of a patient's severed sternum following a partial or median sternotomy comprising:

a first clamp member including an elongate body portion adapted to engage one respective sternal half of the patient's severed sternum and an engagement leg extending from said body portion, said body portion forming a recess;

a second clamp member including an elongate body portion adapted to engage the other respective sternal half of the patient's severed sternum and configured to be at least partially received within said recess, said second clamp member further comprising an engagement leg extending from said body portion;

at least one lock member connected to a top side of said body portion of said first clamp member including a ratchet pawl having at least one inwardly directed ratchet tooth;

at least one corresponding catch member connected to an upper surface of said body portion of said second clamp member including a plurality of ratchet teeth which define a plurality of grooves therebetween;

wherein said ratchet tooth is configured to selectively engage with any one of said plurality of grooves defined between said plurality of ratchet teeth when said body portion of said second clamp member is partially received within the recess of the body portion of the first clamp member to thereby secure the first and second clamp members one to another at any one of a plurality of preselected lateral positions of the clamp members; and a detachment means for releasably engaging said lock member and said catch member to thereby allow said first and second clamp members to be laterally separated from one another.

38. The surgical device of claim 37 wherein said detachment means includes a space between the ratchet pawl and the top side of the body portion of the first clamp member which is sized to allow a surgical instrument access to within the recess in said body portion of said first clamp member to bias said ratchet pawl upwards and away from said ratchet teeth of said second clamp member.

39. A surgical device for reapproximating the sternal halves of a patient's severed sternum following a partial or median sternotomy comprising first and second clamps which are adapted for substantially surrounding an adult patient's sternum and each including respective elongate body portions connected to respective engagement legs, each of said engagement legs including an integral portion which extends towards said other portion of said other engagement leg, wherein said body portion of said first clamp member comprises an integral lock member which is configured to detachably engage with a corresponding catch member connected to the body portion of said second clamp member.

40. A sternal closure device comprising first and second clamps sized and dimensioned to substantially surround an adult patient's sternum, said first clamp having a generally tubular portion and said second clamp having a portion slidably receivable in said tubular portion, and said second clamp is releasably retained within said first clamp.

41. The device of claim 40 wherein each clamp has a generally J-shaped portion.

42. The device of claim 40 wherein each clamp has a generally C-shaped portion.

43. A sternal closure device comprising first and second clamps each having a generally J-shaped portion and including an integral end portion, said first clamp having a generally tubular portion and said second clamp having a portion slidably receivable in said tubular portion, wherein said integral end portion substantially extends towards said other end portion when said first clamp is slidably received in said second clamp, and said second clamp is releasably retained within said first clamp.

44. A sternal closure device comprising first and second clamps each having a generally C-shaped portion and including an integral end portion, said first clamp having a generally tubular portion and said second clamp having a portion slidably receivable in said tubular portion, wherein said integral end portion substantially extends towards said other end portion when said first clamp is slidably received in said second clamp, and said second clamp is releasably retained within said first clamp.

* * * * *